United States Patent [19]
Nudelman et al.

[11] Patent Number: 6,110,970
[45] Date of Patent: Aug. 29, 2000

[54] NITROGEN-CONTAINING OXYALKYLENE ESTERS AND USES THEREOF

[75] Inventors: Abraham Nudelman, Rehovot, Israel; Ada Rephaeli, North Caldwell, N.J.

[73] Assignees: Beacon Laboratories, Inc., Phoenix, Md.; Mor Research Applications, Ltd., Givat Shmuel; Bar-Ilan University, Ramat-Gan, both of Israel

[21] Appl. No.: 08/814,225

[22] Filed: Mar. 11, 1997

[51] Int. Cl.[7] .......................... A01N 37/12; A01N 43/40; A01N 37/02; C07C 229/52

[52] U.S. Cl. .......................... 514/537; 514/356; 514/535; 514/536; 514/547; 546/318; 560/19; 560/170

[58] Field of Search ...................... 560/170, 19; 546/318; 514/356, 535, 536, 537, 547

[56] References Cited

U.S. PATENT DOCUMENTS

| | | |
|---|---|---|
| 2,940,855 | 6/1960 | Beavers et al. . |
| 3,219,630 | 11/1965 | Sidi . |
| 3,293,220 | 12/1966 | Minami et al. . |
| 3,336,262 | 8/1967 | Sidi . |
| 3,720,706 | 3/1973 | Lapporte et al. . |
| 3,812,176 | 5/1974 | Lapporte et al. . |
| 3,931,412 | 1/1976 | Kensler, Jr. et al. . |
| 4,012,526 | 3/1977 | Kensler, Jr. et al. . |
| 4,105,681 | 8/1978 | Bollag et al. . |
| 4,123,552 | 10/1978 | Kensler, Jr. et al. . |
| 4,198,416 | 4/1980 | Koeda et al. . |
| 4,215,215 | 7/1980 | Bollag et al. . |
| 4,541,944 | 9/1985 | Sanderson . |
| 4,545,784 | 10/1985 | Sanderson . |
| 4,613,505 | 9/1986 | Mizushima et al. . |
| 4,699,925 | 10/1987 | Uchida et al. . |
| 4,760,057 | 7/1988 | Alexander . |
| 4,885,311 | 12/1989 | Parish et al. . |
| 4,900,478 | 2/1990 | Gross . |
| 4,916,230 | 4/1990 | Alexander . |
| 5,025,029 | 6/1991 | Perrine . |
| 5,158,773 | 10/1992 | Gross . |
| 5,185,436 | 2/1993 | Villa et al. . |
| 5,196,567 | 3/1993 | Uchida et al. . |
| 5,200,553 | 4/1993 | Nudelman et al. . |
| 5,216,004 | 6/1993 | Perrine . |
| 5,569,675 | 10/1996 | Rephaeli et al. . |
| 5,710,176 | 1/1998 | Rephaeli et al. . |

FOREIGN PATENT DOCUMENTS

| | | |
|---|---|---|
| 0 056 189 A1 | 7/1982 | European Pat. Off. . |
| 79872 A1 | 5/1983 | European Pat. Off. . |
| 0 371 789 A2 | 6/1990 | European Pat. Off. . |
| 1 386 096 | of 1965 | France . |
| 1 540 418 | 9/1968 | France . |
| 58-15912 | 1/1983 | Japan . |
| 63-101348 | 5/1988 | Japan . |
| 1177442 | 1/1970 | United Kingdom . |
| 1 220 447 | 1/1971 | United Kingdom . |
| 1 382 010 | 1/1975 | United Kingdom . |
| 2126082 | 3/1984 | United Kingdom . |
| WO93/19778 | 10/1993 | WIPO . |
| WO98/00127 A1 | 1/1998 | WIPO . |

OTHER PUBLICATIONS

Database CAPLUS on STN, Acc. No. 1988:528504, Thorat et al., 'Polymer–supported reagents: synthesis to hippuric acid esters using anion exchange resin.' Indian J. Chem. Sect. B (1987), 26B(9), p809–810, abstract, 1987.

Brant and Conklin, "Acrolein Diacylates", Chem. Abstracts, vol. 40, p. 3127, 1946.

Carstea, et al., "Analogues of Butyric Acid that Increase the Expression of Transfected DNAs", Biochem. Biophys. Res. Com., vol. 192, No. 2, pp. 649–656, 1993.

Cheng, et al., "Functional Activation of the Cystic Fibrosis Trafficking Mutant deltaF508–CFTR by Overexpression", American Journal of Physiology, vol. 268, No. 4, pp. L615–L624, 1995.

Falch and Krogsgaard–Larsen, "Esters of Isoguvacine as Potential Prodrugs", J. Med. Chem., vol. 24, pp. 285–289, 1981.

Hachisu et al, "Synthesis and Antihypertensive Activity of 5–O–Substituted Derivatives of 5–Hydroxypicolinic Acid", J. Pharm. Dyn., vol. 6, pp. 922–931, 1983.

Ingram and Thomas, "The Electron Impact Induced Fragmentation of Germinal Dialkanoates" Organic Mass Spectrometry, vol. 12, No. 4, pp. 216–221, 1977.

Man, et al., "Boron Fluoride Catalyzed Addition of Aliphatic Anhydrides to Aldehydes", J. Am. Chem. Soc., pp. 847–848, 1950.

Miller, et al., "Clinical Pharmacology of Sodium Butyrate in Patients with Acute Leukemia" Eur. J. Cancer Clin Oncol. vol. 23, No. 9, pp. 1283–1287, 1987.

Mosher and Kehr, "The Oxidation of Aliphatic Esters with Lead Tetraacetate" J. Am. Chem. Soc., vol. 82, pp. 5342–5345, 1960.

Nielsen and Bundgaard, "Evaluation of Glycolamide Esters and Various Other Esters of Aspirin as True Aspirin Prodrugs", J. Medicinal Chem., vol. 32, pp. 727–734, 1989.

Novogrodsky, et al., "Effect of Polar Organic Compounds on Leukemic Cells", Cancer, vol. 51, No. 1, pp. 9–14, 1983.

(List continued on next page.)

*Primary Examiner*—Johann Richter
*Assistant Examiner*—Brian J. Davis
*Attorney, Agent, or Firm*—Kenyon & Kenyon

[57] ABSTRACT

This invention relates to nitrogen-containing oxyalkylene diester compositions for treating disease conditions including cancer and other proliferative diseases. The nitrogen-containing oxyalkylene diesters are represented by the formula

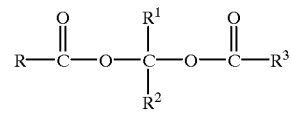

where the nitrogen-containing group is $R_3$ and includes particular alkyl, alkenyl, cycloalkyl, aryl, aralkyl, heterocycloalkyl or heteroaryl groups, which have nitrogen-containing substituents, such as amines, amides, or nitrogen heteroatoms.

16 Claims, 10 Drawing Sheets

OTHER PUBLICATIONS

Nudelman, et al., "Novel Anticancer Prodrugs of Butyric Acid", J. Med. Chem., vol. 35, pp. 687–694, 1992.

Oh, et al., "Convenient Synthesis of Geminal Biscarboxylates: Searching for an Efficient Route to HR 916B", Korean J. Med. Chem., vol. 6, No. 2, pp. 259–262, 1996.

Rephaeli, et al., "Butyrate–Induced Differentiation in Leukemic Myeloid Cells: in vitro and in vivo Studies", International Journal of Oncology, vol. 4, No. 6, pp. 1387–1391, 1994.

Sher et al., "Extended Therapy with Intravenous Arginine Butyrate in Patients with Beta—Hemoglobinopathies", New England Journal of Medicine, vol. 332, No. 24, pp. 1606–1610, 1995.

Smith, et al., "Incorporation of Tributyrin Enhances the Expression of a Reporter Gene in Primary and Immortalized Cell Lines", Biotechniques, vol. 18, pp. 852–855, 1995.

Stamatoyannopoulos, et al. "Therapeutic Approaches to Hemoglobin Switching in Treatment of Hemoglobinopathies", Ann. Rev. Med., vol. 43, pp. 497–522, 1992.

Tang, et al., "Butyrate–Inducible and Tumor–Restricted Gene Expression by Adenovirus Vectors", Cancer Gene Therapy, vol. 1, No. 1, pp. 15–20, 1994.

Tomiska and Spousta, "Low–Molecular Polyoxymethylene Diacetates from Trioxane", Angew. Chem. Internat. Edit., vol. 1, No. 4, p 211, 1962.

NITROGEN-CONTAINING OXYALKYLENE ESTERS AND USES THEREOF

FIELD OF THE INVENTION

This invention relates to compositions for and methods of treating, preventing or ameliorating cancer and other proliferative diseases as well as methods of inducing wound healing, treating cutaneous ulcers, treating gastrointestinal disorders, treating blood disorders such as anemias, immunomodulation, enhancing recombinant gene expression, treating insulin-dependent patients, treating cystic fibrosis patients, inhibiting telomerase activity, treating virus-associated tumors, especially EBV-associated tumors, modulating gene expression and particularly augmenting expression of tumor suppressor genes, inducing tolerance to antigens, treating, preventing or ameliorating protozoan infection or inhibiting histone deacetylase in cells. The compositions of the invention are to and the methods of the invention use nitrogen-containing oxyalkyl esters.

BACKGROUND OF THE INVENTION

Butyric acid (BA) is a natural product. It is supplied to mammals from two main sources: 1) the diet, mainly from dairy fat, and 2) from the bacterial fermentation of unabsorbed carbohydrates in the colon, where it reaches mM concentrations (Cummings, *Gut* 22:763–779, 1982; Leder et al., *Cell* 5:319–322, 1975).

BA has been known for nearly the last three decades to be a potent differentiating and antiproliferative agent in a wide spectra of neoplastic cells in vitro (Prasad, *Life Sci.* 27:1351–1358, 1980). In cancer cells, BA has been reported to induce cellular and biochemical changes, e.g., in cell morphology, enzyme activity, receptor expression and cell-surface antigens (Nordenberg et al., *Exp. Cell Res.* 162:77–85, 1986; Nordenberg et al., *Br. J. Cancer* 56:493–497, 1987; and Fishman et al., *J. Biol. Chem.* 254:4342–4344, 1979).

Although BA or its sodium salt (sodium butyrate, SB) has been the subject of numerous studies, its mode of action is unclear. The most specific effect of butyric acid is inhibition of nuclear deacetylase(s), resulting in hyperacetylation of histones H3 and H4 (Riggs, et al., *Nature* 263:462–464, 1977). Increased histone acetylation, following treatment with BA has been correlated with changes in transcriptional activity and the differentiated state of cells (Thorne et al., *Eur. J. Biochem.* 193:701–713, 1990). BA also exerts other nuclear actions, including modifications in the extent of phosphorylation (Boffa et al., *J. Biol. Chem.* 256:9612–9621, 1981) and methylation (Haan et al., *Cancer Res.* 46:713–716, 1986). Other cellular organelles, e.g., cytoskeleton and membrane composition and function, have been shown to be affected by BA (Bourgeade et al., *J. Interferon Res.* 1:323–332, 1981). Modulations in the expression of oncogenes and suppressor genes by BA were demonstrated in several cell types. Toscani et al., reported alterations in c-myc, p53 thymidine kinase, c-fos and AP2 in 3T3 fibroblasts (*Oncogene Res.* 3:223–238, 1988). A decrease in the expression of c-myc and H-ras oncogenes in B16 melanoma and in c-myc in HL-60 promyelocytic leukemia was also reported (Prasad et al., *Biochem. Cell Biol.* 68:1250–1255, 1992; and Rabizadeh et al., *FEBS Lett.* 328:225–229, 1993).

BA has been reported to induce apoptosis, i.e., programmed cell death. SB has been shown to produce apoptosis in vitro in human colon carcinoma, leukemia and retinoblastoma cell lines (Bhatia et al., *Cell Growth Diff.* 6:937–944, 1995; Conway et al., *Oncol. Res.* 7:289–297, 1993; Hague et al.; *Int. J. Cancer* 60:400–406, 1995). Apoptosis is the physiological mechanism for the elimination of cells in a controlled and timely manner. Organisms maintain a delicate balance between cell proliferation and cell death, which when disrupted can tip the balance between cancer, in the case of over accumulation of cells, and degenerative diseases, in the case of premature cell losses. Hence, inhibition of apoptosis can contribute to tumor growth and promote progression of neoplastic conditions.

The promising in vitro antitumor effects of BA and BA salts led to the initiation of clinical trials for the treatment of cancer patients with observed minimal or transient efficacy [Novogrodsky et al., *Cancer* 51:9–14, 1983; Rephaeli et al., *Intl. J. Oncol.* 4:1387–1391, 1994; Miller et al., *Eur. J. Cancer Clin. Oncol.* 23:1283–1287, 1987].

Clinical trials have been conducted for the treatment of $\beta$-globin disorders (e.g., $\beta$-thalassemia and sickle-cell anemia) using BA salts. The BA salts elevated expression of fetal hemoglobin (HbF), normally repressed in adults, and favorably modified the disease symptoms in these patients (Stamatoyannopouos et al., *Ann. Rev. Med.* 43:497–521, 1992). In this regard, arginine butyrate (AB) has been used in clinical trials with moderate efficacy (Perrine et al., *N. Enq. J. Med.* 328:81–86, 1993; Sher et al., *N. Enq. J. Med.* 332:1606–1610, 1995). The reported side effects of AB included hypokalemia, headache, nausea and vomiting in $\beta$-thalassemia and sickle-cell anemia patients.

Butyric acid derivatives with antitumor activity and immunomodulatory properties have been reported in U.S. Pat. No. 5,200,553 and by Nudelman et al., 1992, *J. Med. Chem.* 35:687–694. The most active buryric acid prodrug reported in these references was pivaloyloxymethyl butyrate (AN-9). Similar compounds are reported for treating hemoglobinopathies (U.S. Pat. No. 5,569,675).

BA and/or its analogues have also been reported to increase the expression of transfected DNA (Carstea et al., 1993, *Biophys. Biochem. Res. Comm.* 192:649; Cheng et al., 1995, *Am. J. Physical* 268:L615–L624) and to induce tumor-restricted gene expression by adenovirus vectors (Tang et al., 1994, *Cancer Gene Therapy* 1:15–20). Tributyrin has been reported to enhance the expression of a reporter gene in primary and immortalized cell lines (Smith et al., 1995, *Biotechniaues* 18:852–835).

However, BA and its salts are normally metabolized rapidly and have very short half-lives in vivo, thus the achievement and maintenance of effective plasma concentrations are problems associated with BA and BA salts, particularly for in vivo uses. BA and BA salts have required large doses to achieve even minimal therapeutic effects. Because of the high dosage, fluid overload and mild alkalosis may occur. Patients receiving BA eminate an unpleasant odor that is socially unacceptable.

While BA salts have been shown to increase HbF expression, and appear to hold therapeutic promise with low toxicity in cancer patients, they nevertheless have shown low potency in in vitro assays and clinical trials. There remains a need to identify compounds as effective or more effective than BA or BA salts as differentiating or antiproliferating agents for the treatment of cancers. Such compounds need to have higher potency than BA without the problems associated with BA (such as bad odor). This need can be addressed by therapeutic compounds that either deliver BA to cells in a longer acting form or which have similar activity as BA but a longer duration of effectiveness in vivo.

The compounds of this invention address these needs and are more potent than BA or BA salts for treating of cancers and other proliferative diseases, for treating gastrointestinal disorders, for wound healing, for treating blood disorders such as thalassemia, sickle cell anemia and other anemias, for modulating an immune response, for enhancing recombinant gene expression, for treating insulin-dependent patients, for treating cystic fibrosis patients, for inhibiting telomerase activity, for treating virus-associated tumors, especially EBV-associated tumors, for modulating gene expression and particularly for augmenting expression of a tumor suppressor gene, for inducing tolerance to an antigen, for treating, preventing or ameliorating protozoan infection and for inhibiting histone deacetylase in cells. For example, one of the advantages of the compounds of the invention is increased water solubility of the free nitrogen-containing oxyalkylene esters compounds of the invention and their salts, and thus easier administration, especially for intravenous administration.

SUMMARY OF THE INVENTION

Accordingly, one embodiment of the present invention is directed to a method of treating preventing or ameliorating cancer and other proliferative disorders using compounds of Formula I represented by:

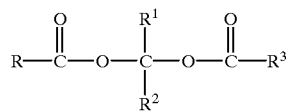

wherein

R is $C_2$ to $C_{10}$ alkyl, alkenyl or alkynyl, any of which can be optionally substituted with aryl, heteroaryl, halo, alkyl, alkoxy, hydroxy, amino, cyano, nitro, trifluoromethyl, acylamino or carbamoyl;

$R^1$ and $R^2$ are independently H, $C_1$–$C_{10}$ alkyl, $C_2$–$C_{10}$ alkenyl, or $C_2$–$C_{10}$ alkynyl, any of which can be optionally substituted with halo, alkoxy, amino, trifluoromethyl, aryl or heteroaryl;

$R^3$ is (1) a nitrogen-containing heterocycloalkyl, heterocycloalkenyl, heteroaryl group or heteroaralkyl group, wherein the heteroaryl group and the heteroaralkyl group can have up to two additional substituents;

(2) an aryl or aralkyl group having one or two nitrogen-containing substituents selected from the group consisting of amino, monoalkylamino, dialkylamino, trialkylammonium salts, acylamino, arylcarbonylamino, alkoxycarbonylamino, formamido, guanidino, ureido, sulfamyl, and alkylsulfonamido, wherein the aryl or aralkyl groups can have up to two additional substituents; or (3) a $C_1$ to $C_{10}$ alkyl, $C_2$ to $C_{10}$ alkenyl, $C_3$ to $C_{10}$ alkynyl or $C_3$ to $C_7$ cycloalkyl group having one or two nitrogen-containing substituents selected from the group consisting of amino, monoalkylamino, dialkylamino, trialkylammonium salts, acylamino, arylcarbonylamino, alkoxycarbonylamino, formamido, guanidino, ureido, sulfamyl, and alkylsulfonamido; and pharmaceutically-acceptable salts thereof;

with the provisos that R is not substituted or unsubstituted n-propyl; and that when R is t-butyl and $R^1$ and $R^2$ are both hydrogen, then $R^3$ can not be 3-aminopropyl or 3-(t-butoxycarbonylamino)propyl. The above compounds are referred to herein as "Formula I compounds."

In addition the invention includes compounds for use in the above method and designated herein as Formula Ia compounds, which are defined the same as in Formula I except that R is substituted or unsubstituted n-propyl (where the substituents are the same as provided for R of Formula I), and that when $R^3$ is $C_1$–$C_{10}$ alkyl, then this moiety can not have an amino substituent.

In a preferred embodiment, the compounds used in the methods of this invention are those of Formula I or Ia wherein R is $C_3$ to $C_6$ alkyl, alkenyl or alkynyl, any of which can be optionally substituted with aryl, heteroaryl, halo, alkyl, alkoxy, hydroxy, amino, cyano, nitro, trifluoromethyl, acylamino or carbamoyl;

$R^1$ and $R^2$ are independently H, $C_1$–$C_{10}$ alkyl, $C_2$–$C_{10}$ alkenyl, or $C_2$–$C_{10}$ alkynyl, any of which can be optionally substituted with halo, alkoxy, amino, trifluoromethyl, aryl or heteroaryl;

$R^3$ is (1) a nitrogen-containing heterocycloalkyl, heteroaryl group or heteroaralkyl group, wherein the heteroaryl group and the heteroaralkyl group can have up to two additional substituents;

(2) an aryl or aralkyl group having one nitrogen-containing substituent selected from the group consisting of amino, monoalkylamino, dialkylamino, trialkylammonium salts, acylamino, arylcarbonylamino, and alkoxycarbonylamino, wherein the aryl or aralkyl groups can have up to one additional substituent; or (3) a $C_1$ to $C_{10}$ alkyl, $C_2$ to $C_{10}$ alkenyl, $C_3$ to $C_{10}$ alkynyl or $C_3$ to $C_7$ cycloalkyl group having one nitrogen-containing substituent selected from the group consisting of amino, monoalkylamino, dialkylamino, trialkylammonium salts, acylamino, arylcarbonylamino and alkoxycarbonylamino; and pharmaceutically-acceptable salts thereof.

In a more preferred embodiment, $R^2$ is H. Yet another preferred embodiment is directed to Formula Ia wherein R is n-propyl;

$R^1$ is H or alkyl and $R^2$ is H;

$R^3$ is (1) a nitrogen-containing heteroaryl group, wherein the heteroaryl group can have one additional substituent;

(2) an aryl group having one nitrogen-containing substituent selected from the group consisting of amino, monoalkylamino, dialkylamino, trialkylammonium salts, and wherein the aryl group can have up to two additional substituents; or (3) a $C_1$ to $C_{10}$ alkyl group having one nitrogen-containing substituent selected from the group consisting of acylamino, arylcarbonylamino and alkoxycarbonylamino; and pharmaceutically-acceptable salts thereof.

The preferred compounds used in the methods of this invention are 4-(butyramido)butyroyloxymethyl butyrate, (BuBuOMB);
4-(butyramido)benzoyloxymethyl butyrate, (BuBOMB);
4-aminobenzoyloxymethyl butyrate, (AmBOMB);
4-aminobenzoyloxymethyl butyrate hydrochloride, (AmBOMB•HCl);
1-(4-aminobenzoyloxy)ethyl butyrate;
3-pyridinecarboxymethyl butyrate, (POMB);
1-(3-pyridinecarboxy)ethyl butyrate; and
(N-methylpyridinium)-3-carboxymethyl butyrate chloride, (MePOMB•Cl).

The compounds of Formula I and Ia are particularly useful for methods of treating, preventing or ameliorating the effects of cancer and other proliferative disorders by acting as anti-proliferative or differentiating agents in subjects afflicted with such anomalies. Such disorders include but are not limited to leukemias, such as acute promyelocytic leukemia, acute myeloid leukemia, and acute myelomonocytic leukemia; other myelodysplastic syndromes, multiple myeloma such as but not limited to breast carcinomas, cervical cancers, melanomas, colon cancers, nasopharyngeal carcinoma, non-Hodgkins lymphoma (NHL), Kaposi's sarcoma, ovarian cancers, pancreatic cancers, hepatocarcinomas, prostate cancers, squamous carcinomas, other dermatologic malignancies, teratocarcinomas, T-cell lymphomas, lung tumors, gliomas, neuroblastomas, peripheral neuroectodermal tumors, rhabdomyosarcomas, and prostate tumors and other solid tumors. It is also possible that compounds of Formula I and Ia have anti-proliferative effects on non-cancerous cells as well, and may be of use to treat benign tumors and other proliferative disorders such as psoriasis. Preferred is the method for treating or ameliorating leukemia, squamous cell carcinoma and neuroblastoma.

The invention is further directed to a method of treating blood disorders by administering a therapeutically-effective amount of a compound of Formula I or Ia to a patient.

The blood disorders treatable in accordance with the invention include, but are not limited to, thalassemias, sickle cell anemias, infectious anemias, aplastic anemias, hypoplastic and hypoproliferative anemias, sideroblastic anemias, myelophthisic anemias, antibody-mediated anemias, anemias due to chronic diseases and enzyme-deficiencies, and anemias due to blood loss, radiation therapy and chemotherapy. In this regard, these methods can include increasing hemoglobin content in blood by administering a therapeutically-effective amount of a compound of Formula I or Ia to a subject.

Another embodiment of the invention is directed to a method of modulating an immune response in a host by administering an amount of a compound of Formula I or Ia effective to modulate said immune response.

Modulation of the immune response includes enhancing cytokine secretion, inhibiting or delaying apoptosis in polymorphonuclear cells, enhancing polymorphonuclear cell function by augmenting hematopoietic growth factor secretion, inducing expression of cell surface antigens in tumor cells, and enhancing progenitor cell recovery after bone marrow transplantation.

Another embodiment of the present invention is directed to methods of treating, preventing or ameliorating cancer and other proliferative disorders by administering a therapeutically-effective amount of a compound of Formula II to a subject suffering from such disorders together with a pharmaceutical agent (e.g., a known antiproliferative, differentiating or oncostatic agent) to thereby enhance the action of these agents.

The compounds of Formula II are represented by the formula

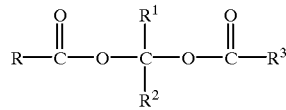

wherein

R is $C_2$ to $C_{10}$ alkyl, alkenyl or alkynyl, any of which can be optionally substituted with aryl, heteroaryl, halo, alkyl, alkoxy, hydroxy, amino, cyano, nitro, trifluoromethyl, acylamino or carbamoyl;

$R^1$ and $R^2$ are independently H, $C_1$–$C_{10}$ alkyl, $C_2$–$C_{10}$ alkenyl, or $C_2$–$C_{10}$ alkynyl, any of which can be optionally substituted with halo, alkoxy, amino, trifluoromethyl, aryl or heteroaryl;

$R^3$ is (1) a nitrogen-containing heterocycloalkyl, heterocycloalkenyl, heteroaryl group or heteroaralkyl group, wherein the heteroaryl group and the heteroaralkyl group can have up to two additional substituents;

(2) an aryl or aralkyl group having one or two nitrogen-containing substituents selected from the group consisting of amino, monoalkylamino, dialkylamino, trialkylammonium salts, acylamino, arylcarbonylamino, alkoxycarbonylamino, formamido, guanidino, ureido, sulfamyl, and alkylsulfonamido, wherein the aryl and aralkyl groups can have up to two additional substituents; or (3) a $C_1$ to $C_{10}$ alkyl, $C_2$ to $C_{10}$ alkenyl, $C_3$ to $C_{10}$ alkynyl or $C_3$ to $C_7$ cycloalkyl group having one or two nitrogen-containing substituents selected from the group consisting of amino, monoalkylamino, dialkylamino, trialkylammonium salts, acylamino, arylcarbonylamino, alkoxycarbonylamino, formamido, guanidino, ureido, sulfamyl, and alkylsulfonamido; and pharmaceutically-acceptable salts thereof.

The compounds of Formula II are nearly the same as covered by the combination of both Formula I and Ia except that the compounds excluded by the provisos therein are included within the class of compounds represented by Formula II. In this regard, the preferred, more preferred and most preferred compounds are the same as for the methods which use Formula I and Ia.

The pharmaceutical agents of the invention for the above method include, but are not limited to, cytokines, interleukins, anti-cancer agents, chemotherapeutic agents, antibodies, conjugated antibodies, immune stimulants, antibiotics, hormone antagonists, and growth stimulants. The compounds of the invention can be administered prior to, after or concurrently with any of the agents.

Yet another embodiment of the invention is directed to a method of ameliorating the effects of a cytotoxic agent which comprises administering a therapeutically-effective amount of a cytotoxic agent with a compound of Formula II to a mammalian patient for a time and in an amount to induce growth arrest of rapidly-proliferating epithelial cells of the patient and thereby protect those cells from the cytotoxic effects of the agent. The cytotoxic agent can be a chemotherapeutic agent, an anticancer agent, or radiation therapy. Rapidly proliferating epithelial cells are found in hair follicles, the gastrointestinal tract and the bladder, for example. Such cells include hair follicle cells, or intestinal cryt cells. Rapidly proliferating cells are also found in the bone marrow and include bone marrow stem cells. In accordance with the invention the cytotoxic agent and the compound of Formula II can be administered simultanously, or the cytotoxic agent can be administered prior to or after the compound of the invention. Administration (simultaneously or separately) can be done systemically or topically as determined by the indication. In addition, when the cytotoxic agent is radiation therapy, the compounds of the invention can be administered to a cancer patient pre- or post-radiation therapy to treat or ameliorate the effects of cancer.

A still further embodiment of the invention is directed to a method of inducing wound healing, treating cutaneous ulcers or treating a gastrointestinal disorder by administering a therapeutically-effective amount of a compound of Formula II to a subject in need of such treatment. The cutaneous ulcers which can be treated in accordance with the methods of the invention include leg and decubitus ulcers, stasis ulcers, diabetic ulcers and atherosclerotic ulcers. With respect to wound healing, the compounds are useful in treating abrasions, incisions, burns, and other wounds. Gastrointestinal disorders treatable by the methods of the invention include colitis, inflammatory bowel disease, Crohn's disease and ulcerative colitis.

A further embodiment of the invention relates to a method of enhancing recombinant gene expression by treating a recombinant host cell containing an expression system for a mammalian gene product of interest with an expression-enhancing amount of a compound of Formula II, wherein said gene product is encoded by a butyric acid-responsive gene. The host cells can be mammalian cells, insect cells, yeast cells or bacterial cells and the correspondingly known expression systems for each of these host cells. The gene product can be any protein or peptide of interest, expression of which can be regulated or altered by butyric acid or a butyric acid salt. A butyric acid-responsive gene is a gene that has a promoter, enhancer element or other regulon that modulates expression of the gene under its control in response to butyric acid or a salt of butyric acid. For example, gene products contemplated for regulation in accordance with the invention include but are not limited to tumor suppressor genes (such as p53) and the γ-globin chain of fetal hemoglobin.

Yet a further embodiment of the invention is directed to a method of treating, preventing or ameliorating symptoms in insulin-dependent patients by administering an amount of a compound of Formula II effective to enhance insulin expression.

Yet another embodiment of the invention relates to a method of treating, preventing or ameliorating symptoms in cystic fibrosis patients by administering an amount of a compound of Formula II effective to enhance chloride channel expression.

Still another method of the invention is directed to a method of inhibiting telomerase activity in cancer cells by administering a telomerase-inhibiting amount of a compound of Formula II to the cells, wherein the amount is effective to decrease the telomerase activity of the cells and thereby inhibit the malignant progression of the cells. This method can be applied to in vivo or in vitro cells.

Another embodiment of this invention is directed to a method of treating, preventing or ameliorating virus-associated tumors by pre-, post or co-administering a therapeutically-effective amount of a compound of Formula II with a therapeutically-effective amount of an antiviral agent. Antiviral agents contemplated for use in the invention include ganciclovir, acyclovir and famciclovir, and preferably ganciclovir. The virus-associated tumors which can be treated, prevented or ameliorated in accordance with the invention include, but are not limited to, EBV-associated malignancy, Kaposi's sarcoma, AIDS-related lymphoma, hepatitis B-associated malignancy or hepatitis C associated malignancy. EBV-associated malignancies include nasopharyngeal carcinoma and non-Hodgkins' lymphoma and are preferred embodiments of the invention.

Further still the invention provides a method of modulating gene expression by treating a host or host cells with an amount of a compound of Formula II effective to enhance, augment or repress the expression of a gene of interest, preferably a butyric acid responsive gene. When expression of the gene of interest is to be enhanced or augmented, the gene can encode a gene product which is or acts as a repressor of another gene, a tumor suppressor, an inducer of apoptosis or an inducer of differentiation. When expression of the gene of interest is to be repressed, the gene can encode a gene product which is or acts as an oncogene or an inhibitor of apoptosis. For example, the bcl-2 gene encodes an inhibitor of apoptosis.

More particularly, the invention is directed to a method of augmenting gene expression, especially of a tumor suppressor gene, a butyric acid-responsive gene or a fetal hemoglobin gene, by treating a host or host cells with an expression-enhancing amount of a compound of Formula II. Preferably the host is a cancer patient. This method of the invention thus includes augmenting tumor suppressor gene expression in conjunction with ex vivo or in vivo gene therapy, i.e., the compound of the invention can be co-administered to the host during administration of gene therapy vectors or administration of the ex vivo transfected cells. Similarly, the compounds of the invention can be used to treat cells during the transfection step of ex vivo gene therapy. The hosts of the method therefore include cancer patients or other patients under going gene therapy. The host cells of the invention include hematopoietic cells such as stem cells and progenitor cells, e.g., or any other cell type used in ex vivo gene therapy.

Yet another embodiment of the invention is directed to a method of inducing tolerance to an antigen which comprises administering a therapeutically-effective amount of compound of Formula II. Preferably the antigen is a self-antigen. For example, the self antigen can be associated with an autoimmune disease such as systemic lupus erythromatosis, rheumatoid arthritis, multiple sclerosis or diabetes. Alternatively, tolerance can be induced to one or more antigens present on a transplanted organ or cells.

Yet further the invention is directed to a method for treating, preventing, or ameliorating protozoan infection in a subject which comprises administering to said subject an effective amount of a compound of Formula II. The protozoan infections treatable in accordance with the invention include, but are not limited to, malaria, cryptosporidiosis, toxoplasmosis, or coccidiosis.

Still further the invention is directed to a method of inhibiting histone deacetylase in cells which comprises administering an effective amount of a compound of Formula II to said cells.

The invention is also directed to compounds represented by the formula:

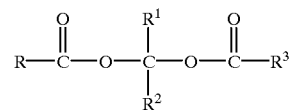

wherein

R is $C_2$ to $C_{10}$ alkyl, alkenyl or alkynyl, any of which can be optionally substituted with aryl, heteroaryl, halo, alkyl, alkoxy, hydroxy, amino, cyano, nitro, trifluoromethyl, acylamino or carbamoyl;

$R^1$ and $R^2$ are independently H, $C_1$–$C_{10}$ alkyl, $C_2$–$C_{10}$ alkenyl, or $C_2$–$C_{10}$ alkynyl, any of which can be optionally substituted with halo, alkoxy, amino, trifluoromethyl, aryl or heteroaryl;

$R^3$ is (1) a nitrogen-containing heterocycloalkyl or heteroaryl group, wherein the heteroaryl group can have up to two additional substituents;

(2) an aryl or aralkyl group having one or two nitrogen-containing substituents selected from the group consisting of amino, monoalkylamino, dialkylamino, trialkylammonium salts, and acylamino, wherein the aryl or aralkyl group can have up to two additional substituents; or (3) a $C_1$ to $C_{10}$ alkyl, $C_2$ to $C_{10}$ alkenyl, or $C_5$ to $C_7$ cycloalkyl group having one or two nitrogen-containing substituents selected from the group consisting of amino, monoalkylamino, dialkylamino, trialkylammonium salts, acylamino, arylcarbonylamino and ureido; and pharmaceutically-acceptable salts thereof;

with the provisos that R is not substituted or unsubstituted n-propyl; that when R is t-butyl and $R^1$ and $R^2$ are both hydrogen, then $R^3$ can not be 3-aminopropyl or 3-(t-butoxycarbonylamino)propyl; that when R is isopropyl and $R^1$ and $R^2$ are both hydrogen, then $R^3$ can not be 2-amino-6-chlorophenyl or 8-(3,7-dichloro-quinoline); and that when R is isopropyl, $R^1$ is hydrogen, and $R^2$ is methyl, then $R^3$ can not be 4-(methylamino)cyclohexane.

The above compounds are referred to herein as "Formula III compounds."

In addition, the invention is directed to compounds designated as Formula IIIa which are the same as Formula I except that R is substituted or unsubstituted n-propyl (where the substituents are the same as provided for R of Formula III), and that when $R^3$ is $C_1$–$C_{10}$ alkyl, then this group can not have an amino substituent.

In a preferred embodiment, the compounds of the invention are those of Formula III and IIIa wherein R is $C_3$ to $C_6$ alkyl, alkenyl or alkynyl, any of which can be optionally substituted with aryl, heteroaryl, halo, alkyl, alkoxy, hydroxy, amino, cyano, nitro, trifluoromethyl, acylamino or carbamoyl;

$R^1$ and $R^2$ are independently H, lower alkyl or lower alkenyl;

$R^3$ is (1) a nitrogen-containing heterocycloalkyl or heteroaryl group, wherein the heteroaryl group can have up to two additional substituents;

(2) an aryl or aralkyl group having one nitrogen-containing substituent selected from the group consisting of amino, monoalkylamino, dialkylamino, trialkylammonium salts, acylamino, arylcarbonylamino, and alkoxycarbonylamino, wherein the aryl or aralkyl group can have up to one additional substituent; or (3) a $C_1$ to $C_{10}$ alkyl, $C_2$ to $C_{10}$ alkenyl, $C_3$ to $C_{10}$ alkynyl or $C_3$ to $C_7$ cycloalkyl group having one nitrogen-containing substituent selected from the group consisting of amino, monoalkylamino, dialkylamino, trialkylammonium salts, acylamino, arylcarbonylamino and alkoxycarbonylamino; and pharmaceutically-acceptable salts thereof.

In a more preferred embodiment, $R^2$ is H. Yet another preferred embodiment is directed to Formula IIIa wherein R is n-propyl;

$R^1$ is H or alkyl and $R^2$ is H;

$R^3$ is (1) a nitrogen-containing heteroaryl group, wherein said heteroaryl group can one additional substituent;

(2) an aryl group having one nitrogen-containing substituent selected from the group consisting of amino, monoalkylamino, dialkylamino, trialkylammonium salts, and wherein the aryl group can have up to two additional substituents; or (3) a $C_1$ to $C_{10}$ alkyl group having one nitrogen-containing substituent selected from the group consisting of acylamino, arylcarbonylamino and alkoxycarbonylamino.

The preferred compounds of the invention are BuBuOMB, BuBOMB, AmBOMB, AmBOMB•HCl POMB, MePOMB•Cl, 1-(4-aminobenzoyloxy)ethyl butyrate and 1-(3-pyridinecarboxy)ethyl butyrate.

Another embodiment of the present invention is drawn to pharmaceutical compositions comprising a therapeutically effective amount of a compound of Formula III or IIIa and a pharmaceutically effective carrier or diluent.

A further embodiment of the present invention is directed to pharmaceutical compositions comprising a therapeutically effective amount of a combination of a compound of Formula III or IIIa with other anti-cancer or antineoplastic agents together with a pharmaceutically effective carrier or diluent.

DETAILED DESCRIPTION OF THE INVENTION

Figure 1A:
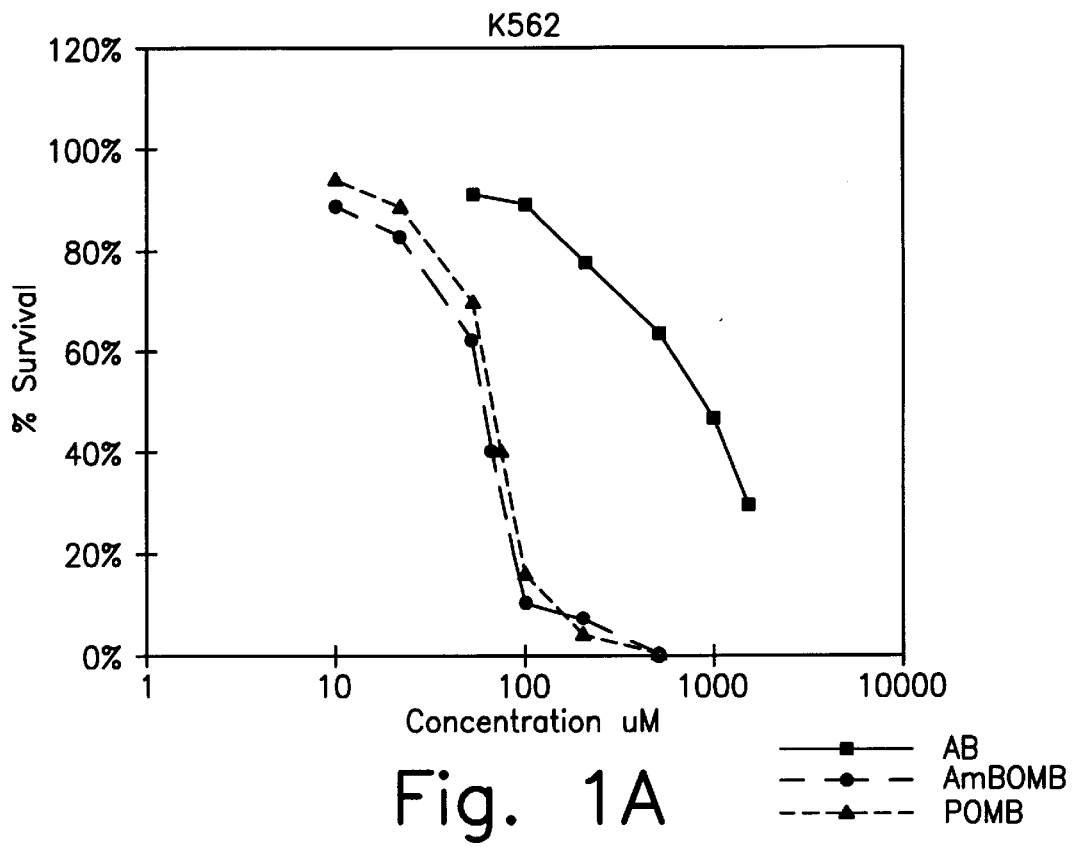
FIG. 1 is a graphic illustration showing the in vitro inhibition of cellular growth (clonogenicity) by AB, AmBOMB or POMB on established human neuroblastoma cell lines as a function of concentration (in $\mu M$).
Figure 1B:
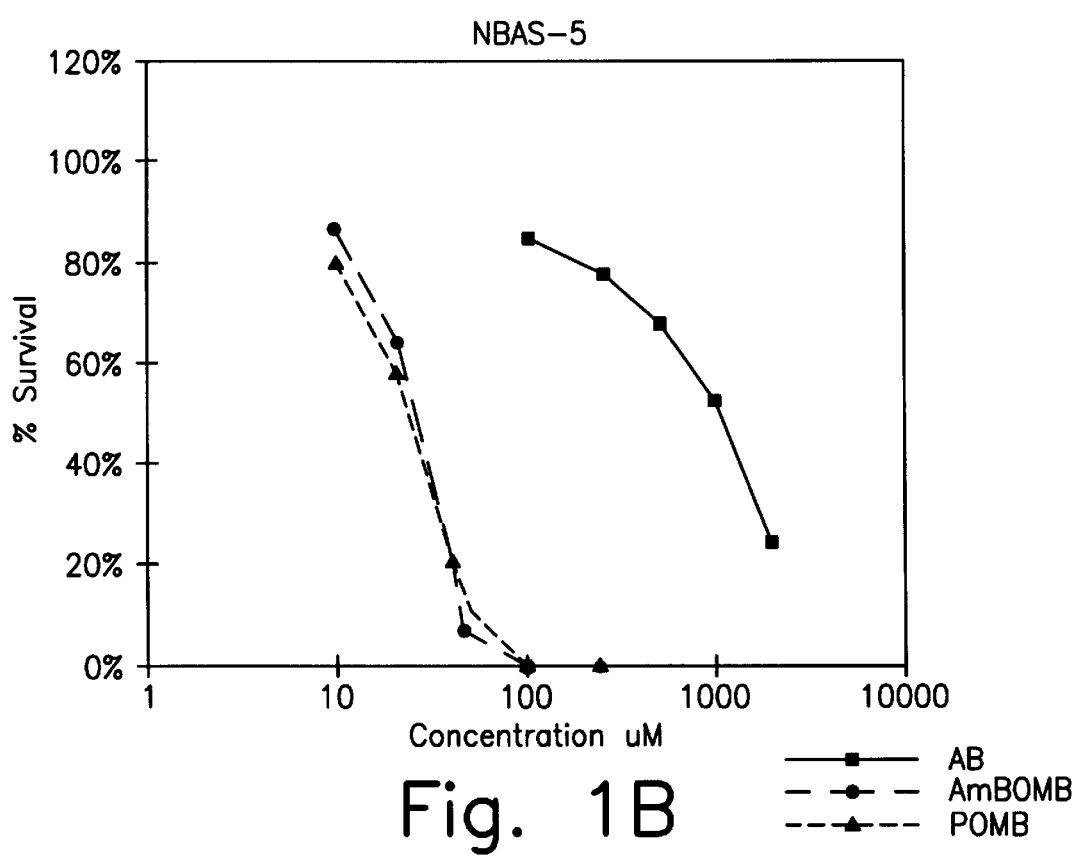
Figure 1C:
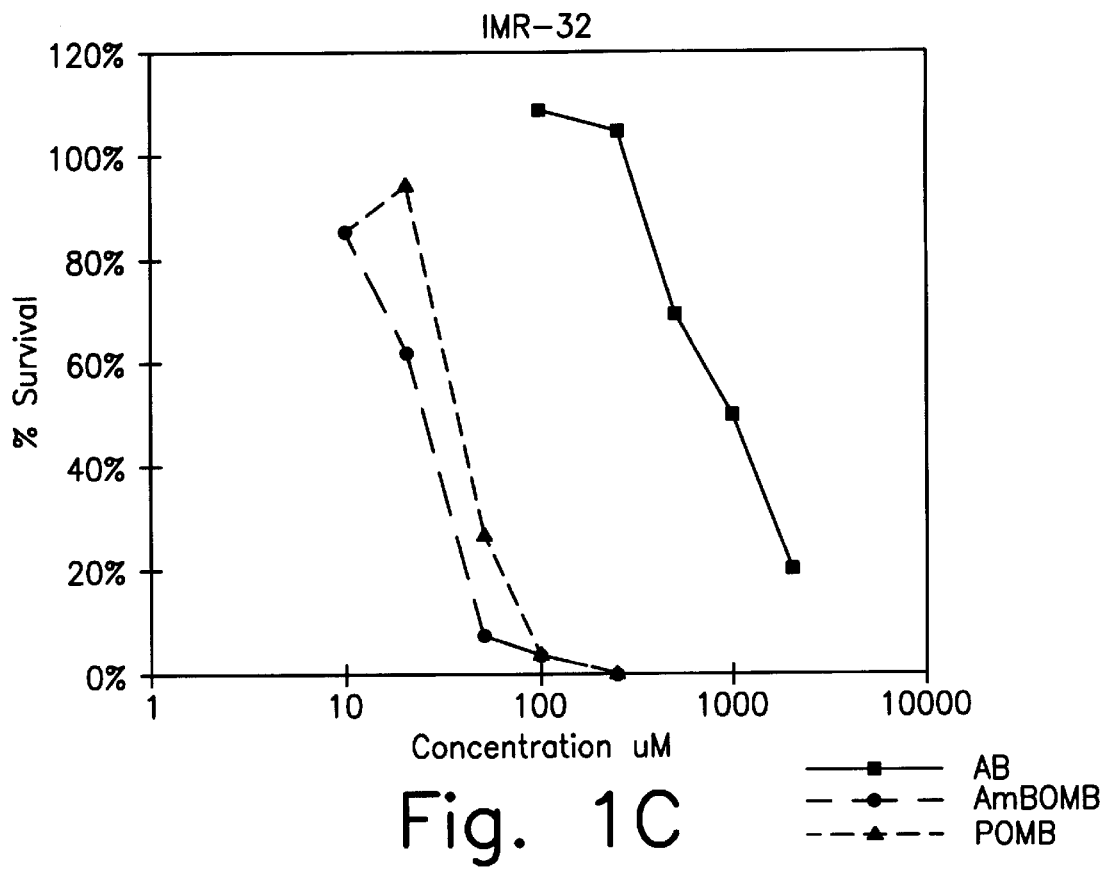
Figure 1D:
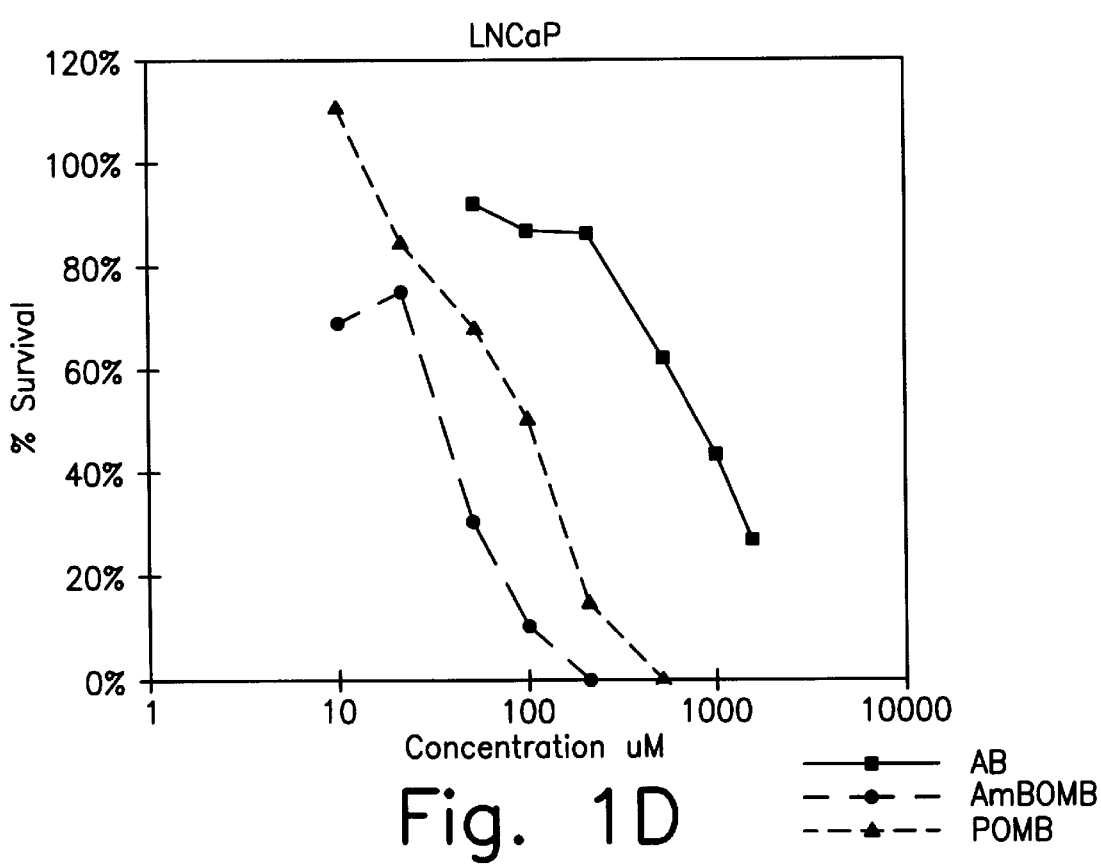

The compounds herein described may have asymmetric centers. All chiral, diastereomeric, and racemic forms are included in the present invention. Many geometric isomers of olefins and the like can also be present in the compounds described herein, and all such stable isomers are contemplated in the present invention.

By "stable compound" or "stable structure" is meant herein a compound that is sufficiently robust to survive isolation to a useful degree of purity from a reaction mixture, and formulation into an efficacious therapeutic agent.

As used herein, "alkyl" means both branched- and straight-chain, saturated aliphatic hydrocarbon groups having the specified number of carbon atoms. As used herein "lower alkyl" means an alkyl group having 1 to 5 carbon atoms. As used herein, "alkenyl" means hydrocarbon chains of either a straight or branched configuration and one or more unsaturated carbon-carbon bonds, such as ethenyl, propenyl, and the like. "Lower alkenyl" is an alkenyl group having 2 to 6 carbon atoms. As used herein, "alkynyl" means hydrocarbon chains of either a straight or branched configuration and one or more carbon-carbon triple bonds, such as ethynyl, propynyl and the like. "Lower alkynyl" is an alkynyl group having 2 to 6 carbon atoms. When the number of carbon atoms is not specified, then alkyl, alkenyl and alkynyl means lower alkyl, lower alkenyl and lower alkynyl, respectively.

As used herein, "aryl" includes "aryl" and "substituted aryl." Thus "aryl" of this invention means any stable 6- to 14-membered monocyclic, bicyclic or tricyclic ring, containing at least one aromatic carbon ring, for example, phenyl, naphthyl, indanyl, tetrahydronaphthyl (tetralinyl) and the like. The presence of substitution on the aryl group is optional, but when present, the substituents can be halo, alkyl, alkoxy, hydroxy, amino, cyano, nitro, trifluoromethyl, acylamino or carbamoyl.

As used herein, the term "heteroaryl" includes "heteroaryl" and "substituted heteroaryl." Thus "heteroaryl" of this invention means a stable 5- to 10-membered monocyclic or bicyclic heterocyclic ring which is aromatic, and which consists of carbon atoms and from 1 to 3 heteroatoms selected from the group consisting of N, O and S and wherein the nitrogen may optionally be quaternized, and including any bicyclic group in which any of the above-defined heteroaryl rings is fused to a benzene ring. The heteroaryl ring may be attached to its pendant group at any heteroatom or carbon atom which results in a stable structure. The presence of substitution on the heteroaryl group is optional and can be on a carbon atom, a nitrogen atom or other heteroatom if the resulting compound is stable and all the valencies of the atoms have been satisfied. When present, the substituents of the substituted heteroaryl groups are the same as for the substituted aryl groups and also include alkylammonium salts when the substituent is an alkyl group attached to the nitrogen atom of the heteroaryl ring. These quarternized ammonium salts include halides, hydrohalides, sulfates, methosulfates, methanesulfates, toluenesulfates, nitrates, phosphates, maleates, acetates, lactates or any other pharmaceutically acceptable salt. Examples of heteroaryl groups include, but are not limited to, pyridyl, pyrimidinyl, furanyl, thienyl, pyrrolyl, pyrazolyl, imidazolyl, tetrazolyl, benzofuranyl, benzothienyl, indolyl, indolenyl, quinolinyl, isoquinolinyl and benzimidazolyl.

As used herein, "aralkyl" and "heteroaralkyl" refer to an aryl or heteroaryl group attached to an alkyl group. The aryl and heteroaryl groups of this moiety can optionally be substituted in accordance with the definitions herein. Examples of heteroaralkyl groups include but are not limited to 2-, 3-, or 4-pyridylmethyl and 3-(2-, 3- or 4- pyridyl) propyl and the like.

The term "substituted", as used herein, means that one or more hydrogens on the designated atom are replaced with a selection from the indicated groups, provided that the designated atom's normal valency is not exceeded, and that the substitution results in a stable compound.

The substituents of the invention include, as indicated, halo, hydroxy, alkyl, alkoxy, amino, cyano, nitro, trifluoromethyl, aryl, heteroaryl, monoalkylamino, dialkylamino, trialkylammonium and salts thereof, carbamoyl, acylamino, arylcarbonylamino, alkoxycarbonylamino, formamido, guanidino, ureido, sulfamyl, and alkylsulfonamido. These groups can be substituents for alkyl, alkenyl, alkynyl, cycloalkyl, aryl, aralkyl, heteroaryl and heteroaralkyl groups as indicated in accordance with the invention. A "halo" group is a halogen, and includes fluoro, chloro, bromo and iodo groups. The term "alkoxy" refers to an alkyl group having at least one oxygen substituent represented by R—O—. The group "acylamino" is represented by the formula R—C(O)—NH— where R is alkyl. "Arylcarbonylamino" and "alkoxycarbonylamino" are similar to acylamino except that the R is aryl or alkoxy, respectively.

As used herein, "therapeutically-effective amount" refers to that amount necessary to administer to a host to achieve an anti-tumor effect; to induce differentiation and/or inhibition of proliferation of malignant cancer cells, benign tumor cells or other proliferative cells; to aid in the chemoprevention of cancer; to promote wound healing; to treat a gastrointestinal disorder; to treat a blood disorder or increase the hemoglobin content of blood; to modulate an immune response; to enhance recombinant gene expression; to modulate gene expression; to augment expression of tumor suppressor genes; to enhance insulin expression; to enhance chloride channel expression; to induce tolerance to an antigen; to treat, prevent or ameliorate protozoan infection; or to inhibit histone deacetylase in cells. Methods of determining therapeutically-effective amounts are well known.

When the therapeutic or effective amount of the compound is for treating, preventing or ameliorating cancer or other proliferative disorder, then that amount can be an amount effective to inhibit histone deacetylase in the subject, patient or cancerous cells. Similarly, when the therapeutic or effective amount of the compound is for treating, preventing, or ameliorating protozoan infection then that amount can be an amount effective to inhibit protozoan histone deacetylase in the subject, patient or cancerous cells.

As used herein, "pharmaceutically acceptable salts" refer to derivatives of the disclosed compounds that are modified by making acid or base salts. Examples include, but are not limited to, mineral or organic acid salts of basic residues such as amines; alkali or organic salts of acidic residues such as carboxylic acids, and the like. Pharmaceutically acceptable salts include, but are not limited to, hydrohalides, sulfates, methosulfates, methanesulfates, toluenesulfonates, nitrates, phosphates, maleates, acetates, lactates and the like.

Pharmaceutically-acceptable salts of the compounds of the invention can be prepared by reacting the free acid or base forms of these compounds with a stoichiometric or greater amount of the appropriate base or acid in water or in an organic solvent, or in a mixture of the two; generally, nonaqueous media like ether, ethyl acetate, ethanol, isopropanol, or acetonitrile are preferred. The salts of the invention can also be prepared by ion exchange, for example. Lists of suitable salts are found in *Remington's Pharmaceutical Sciences,* 17th ed., Mack Publishing Company, Easton, Pa., 1985, p. 1418, the disclosure of which is hereby incorporated by reference in its entirety.

The "pharmaceutical agents" for use in the methods of the invention related to the coadministration of compounds of Formula II and Formula III, include but are not limited to anticancer agents as well as differentiating agents. For example, the pharmaceutical agent can be a cytokine, an interleukin, an anti-cancer agent, a chemotherapeutic agent, an antibody, a conjugated antibody, an immune stimulant, an antibiotic, a hormone antagonist or a growth stimulant. The pharmaceutical agent can also be a cytotoxic agent. Cytotoxic agents include antiviral nucleoside antibiotics such as ganciclovir, acyclovir, and famciclovir. Cytotoxic agents can also include radiation therapy.

As used herein, the "chemotherapeutic agents" include but are not limited to alkylating agents, purine and pyrimidine analogs, vinca and vinca-like alkaloids, etoposide and etoposide-like drugs, corticosteroids, nitrosoureas, antimetabolites, platinum-based cytotoxic drugs, hormonal antagonists, anti-androgens and antiestrogens.

The "cytokines" for use herein include but are not limited to interferon, preferably α, β or γ interferon, as well as IL-2, IL-3, G-CSF, GM-CSF and EPO.

As used herein, an "immune stimulant" is a substance such as C. parvum or sarcolectin which stimulates a humoral or cellular component of the immune system.

The chemotherapeutic agents of the invention include but are not limited to tamoxifen, doxorubicin, L-asparaginase, dacarbazine, amsacrine, procarbazine, hexamethylmelamine, mitoxantrone and gemcitabine.

SYNTHETIC METHODS

The compounds of the present invention can generally be prepared by any method known in the art. For example, the compounds of the invention can be made by reacting the acid RCOOH with a reagent of the formula

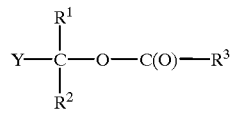

or by similar reactions between any of the appropriate acids and the appropriate alkyl halides in the presence of a base, where Y is a leaving group such as halogen, methanesulfonate or p-toluenesulfonate and R, $R^1$, $R^2$ and $R^3$ are as defined herein. The above reagents are readily prepared according to literature procedures, see for example, Nudelman et al., J. Med. Chem. 35:687–694, 1992, and Japanese patent 07033709 (1995). The base can be a trialkylamine, pyridine, an alkali metal carbonate or other suitable base. The reaction can be carried out in the presence or absence of an inert solvent. Suitable solvents include, for example, acetone, benzene, toluene, tetrahydrofuran, ethyl acetate, acetonitrile, dimethylformamide, dimethyl sulfoxide, chloroform, dioxan or 1,2-dichloroethane.

The procedures outlined above can be improved by one skilled in the art by, for instance, changing the temperature, duration, stoichiometry or other parameters of the reactions. Any such changes are intended to fall within the scope of this invention.

ACTIVITY

The activities of the compounds of the invention can be measured using generally-accepted techniques known to those skilled in the art consistent with the activity of interest. For example, the activity of compounds useful as differentiating agents can be measured using standard methodology of the nitro-blue tetrazolium reduction assay (e.g., Rabizadeh et al., FEBS Lett. 328:225–229, 1993; Chomienne et al., Leuk. Res. 10:631, 1986; and Breitman et al. in Methods for Serum-free Culture of Neuronal and Lymphoid Cells, Alan R. Liss, NY, p. 215–236, 1984 which are hereby incorporated by reference in their entirety) and as described below. This in vitro assay has been deemed to be predictive and in fact correlative with in vivo efficacy (Castaigne et al., Blood 76:1704–1709, 1990).

Another assay which is predictive of differentiating activity is the morphological examination for the presence of Auer rods and/or specific differentiation cell surface antigens in cells collected from treatment groups, as described in Chomienne et al., (Blood 76:1710–1717, 1990 which is hereby incorporated by reference in its entirety) and as described below.

The compounds of the present invention also have antiproliferative and anti-tumor activity. The anti-proliferation activity of compounds of the present invention can be determined by methods generally known to those skilled in the art. Generally-accepted assays for measuring viability and anti-proliferative activity are the trypan blue exclusion test and incorporation of tritiated thymidine, also as described by Chomienne, et al., above, which is incorporated herein by reference. Other assays which predict and correlate antitumor activity and in vivo efficacy are the human tumor colony forming assay described in Shoemaker et al., Can. Res. 45:2145–2153, 1985, and inhibition of telomerase activity as described by Hiyayama et al., J. Natl. Cancer Inst. 87:895–908, 1995, which are both incorporated herein by reference in their entirety. These assays are described in further detail below.

Cell Cultures

Human promyelocytic leukemia cells (HL-60), human pancreatic carcinoma cells (PaCa-2) and human breast adenocarcinoma cells, pleural effusion cells (MCF-7) can be cultured as follows. Cells are grown in RPMI media with 10% FCS, supplemented with 2 mM glutamine and incubated at 37° C. in a humidified 5% $CO_2$ incubator. Alternatively, cells can be grown in any other appropriate growth medium and conditions which supports the growth of the cell line under investigation. Viability can be determined by trypan blue exclusion. Cells are exposed to a test compound, cultures are harvested at various time points following treatment and stained with trypan blue.

Cellular Staining to Detect Differentiation

Lipid staining and/or immunochemical staining of casein can be used as a marker for cellular differentiation of breast cancer cells (Bacus et al., Md. Carcin. 3:350–362, 1990). Casein detection can be done by histochemical staining of breast cancer cells using a human antibody to human casein as described by Cheung et al., J. Clin. Invest. 75:1722–1728, which is incorporated by reference in its entirety.

Nitro-Blue Tetrazolium (NBT) Assay:

Cell differentiation of myeloid leukemia cells can be evaluated, for example, by NBT reduction activity as follows. Cell cultures are grown in the presence of a test compound for the desired time period. The culture medium is then brought to 0.1% NBT and the cells are stimulated with 400 mM of 12-O-tetradecanoyl-phorbol-13-acetate (TPA). After incubation for 30 min at 37° C., the cells are examined microscopically by scoring at least 200 cells. The capacity for cells to reduce NBT is assessed as the percentage of cells containing intracellular reduced black formazan deposits and corrected for viability.

Cell Surface Antigen Immunophenotyping

Cell surface antigen immunotyping can be conducted using dual-color fluorescence of cells gated according to size. The expression of a panel of antigens from early myeloid (CD33) to late myeloid can be determined as described in Warrell, Jr. et al., New Engl. J. Med. 324:1385–1392, 1992, which is incorporated by reference herein in its entirety.

Apoptosis Evaluation

Apoptosis can be evaluated by DNA fragmentation, visible changes in nuclear structure or immunocytochemical analysis of Bcl-2 expression.

DNA fragmentation can be monitored by the appearance of a DNA ladder on an agarose gel. For example, cellular DNA is isolated and analyzed by the method of Martin et al., J. Immunol., 145:1859–1867, 1990 which is incorporated by reference herein in its entirety.

Changes in nuclear structure can be assessed, for example, by acridine orange staining method of Hare et al., J. Hist. Cyt., 34:215–220, 1986 which is incorporated by reference herein in its entirety.

Immunological detection of Bcl-2 can be performed on untreated cells and cells treated with the test compound. HL-60 cells are preferred but other cell lines capable of expressing Bcl-2 can be used. Cytospins are prepared and the cells are fixed with ethanol. Fixed cells are reacted overnight at 4° C. with the primary monoclonal antibody, anti-Bcl-2 at a dilution of 1:50. Staining is completed to visualize antibody binding, for example, using Strep A-B Universal Kit (Sigma) in accordance with the manufacturer's instructions. Identically-treated cells which received no primary antibody can serve as a non-specific binding control. Commercial kits are also available and can be used for detecting apoptosis, for example, Oncor's Apop Tag®.

Modulation of Gene Expression

The levels of expression from oncogene and tumor suppressor genes can be evaluated by routine methods known in the art such as Northern blotting of RNA, immunoblotting of protein and PCR amplification.

Mouse Cancer Model

Compounds can be examined for their ability to increase the life span of animals bearing B16 melanomas, Lewis lung carcinomas and myelomonocytic leukemias as described in Nudelman et al., J. Med. Chem. 35:687–694, 1992, or Rephaeli et al., Int. J. Cancer 49:66–72, 1991, which are incorporated by reference herein in their entireties.

For example, the efficacy of compounds of the present invention in a leukemia model can be tested as follows: Balb/c mice are injected with WEHI cells and a test compound or control solution is administered the following day. The life span of the treated animals is compared to that of untreated animals.

The efficacy of compounds of the present invention on primary tumors can also be tested with subcutaneously implanted lung carcinoma or B16 melanoma by measuring the mass of the tumor at the site of implantation every two weeks in control and treated animals.

The efficacy of compounds in xenografts can be determined by implanting the human tumor cells subcutaneously into athymic mice. Human tumor cell lines which can be used include, but are not limited to, prostate carcinoma (human Pc-3 cells), pancreatic carcinoma (human Mia PaCa cells), colon adenocarcinoma (human HCT-15 cells) and mammary adenocarcinoma (human MX-1 cells). Treatment with control solution or a test compound of the invention begins, for example, when tumors are approximately 100 mg. Anti-tumor activity is assessed by measuring the delay in tumor growth, and/or tumor shrinking and/or increased survival of the treated animals relative to control animals.

Telomerase Activity

High levels of telomerase activity is associated with the high proliferation rate found in cancer cells. Compounds which inhibit telomerase activity results in inhibition of cancer cell growth and de-differentiation. Commercially available telomerase assays can thus be used to assess the anticancer activities of compounds on cancer cell lines.

Chemoprevention

The chemoprevention activity of the compounds of the invention can be determined in the two-stage mouse carcinogenesis model of Nishimo et al. (supra). In this regard, AmBOMB is expected to have good chemoprevention activity since it can release two active compounds when hydrolyzed by cellular or blood esterases, namely butyric acid and para-aminobenzoic acid (PABA). PABA is associated with antimutagenic activity. (Semenov et al., 1994, Vopr. Med. Khim. 40:48).

Assay of Compounds

Compounds of the invention, their salts or metabolites, can be measured in a biological sample by any method known to those skilled in the art of pharmacology, clinical chemistry or the like. Such methods for measuring these compounds are standard methods and include, but are not limited to high performance liquid chromatography (HPLC), gas chromatography (GC), gas chromatography mass spectroscopy (GC-MS), radioimmunoassay (RIA), and others.

Dosage and Formulation

The compounds of the present invention can be administered to a mammalian patient to treat cancer or in any other method of the invention which involves treating a patient by any means that produces contact of the active agent with the agent's site of action in the body of the subject. Mammalian patients include humans and domestic animals. The compounds of the invention can be administered by any conventional means available for use in conjunction with pharmaceuticals, either as individual therapeutic agents or in a combination of therapeutic agents. The compounds can be administered alone, but are generally administered with a pharmaceutical carrier selected on the basis of the chosen route of administration and standard pharmaceutical practice. The pharmaceutical compositions of the invention may be adapted for oral, parenteral, transdermal, transmucosal, rectal or intranasal administration, and may be in unit dosage form, as is well known to those skilled in the pharmaceutical art. The term "parenteral" as used herein includes subcutaneous, intravenous, intramuscular, or intrasternal injection or infusion techniques.

The appropriate dosage administered in any given case will, of course, vary depending upon known factors, such as the pharmacodynamic characteristics of the particular agent and its mode and route of administration; the age, general health, metabolism, weight of the recipient and other factors which influence response to the compound; the nature and extent of the symptoms; the kind of concurrent treatment; the frequency of treatment; and the effect desired. A daily dosage of active ingredient can be expected to be about 10 to 10,000 milligrams per meter$^2$ of body mass (mg/m$^2$), with the preferred dose being 50–5,000 mg/m$^2$ body mass.

Dosage forms (compositions suitable for administration) contain from about 1 mg to about 1 g of active ingredient per unit. In these pharmaceutical compositions the active ingredient will ordinarily be present in an amount of about 0.5–95% by weight based on the total weight of the composition.

The active ingredient can be administered orally in solid or semi-solid dosage forms, such as for example hard or soft-gelatin capsules, tablets, and powders, or in liquid dosage forms, such as elixirs, syrups, disperse powders or granules, emulsions, and aqueous or oily suspensions. It can also be administered parenterally, in sterile liquid dosage forms. Other dosage forms include transdermal administration via a patch mechanism or ointment.

Compositions intended for oral use may be prepared according to any methods known to the art for the manufacture of pharmaceutical compositions and such compositions may contain one or more agents including sweetening agents, flavoring agents, coloring agents, and preserving agents in order to provide a pharmaceutically elegant and palatable preparation.

Tablets contain the active ingredient in admixture with non-toxic pharmaceutically acceptable excipients which are suitable for the manufacture of tablets. Such excipients may include, for example, inert diluents, such as calcium phosphate, calcium carbonate, sodium carbonate, sodium phosphate, or lactose; granulating disintegrating agents, for example, maize starch or alginic acid; binding agents, such as starch, gelatin, or acacia; and lubricating agents, for example, magnesium stearate, stearic acids or talc. Compressed tablets may be uncoated or may be sugar coated or film coated by known techniques to mask any unpleasant taste and protect the tablet from the atmosphere, or enteric coated for selective disintegration and adsorption in the gastrointestinal tract.

Hard gelatin capsules or liquid filled soft gelatin capsules contain the active ingredient and inert powdered or liquid carriers, such as, but not limited to calcium carbonate, calcium phosphate, kaolin, lactose, lecithin starch, cellulose derivatives, magnesium stearate, stearic acid, arachis oil, liquid paraffin, olive oil, pharmaceutically-accepted synthetic oils and other diluents suitable for the manufacture of capsules. Both tablets and capsules can be manufactured as sustained release-products to provide for continuous release of medication over a period of hours.

Aqueous suspensions contain the active compound in admixture with excipients suitable for the manufacture of aqueous suspensions. Such excipients are suspending agents, e.g., sodium carboxymethylcellulose, methylcellulose, hydroxypropylmethylcellulose, sodium alginate, polyvinylpyrrolidone, gum tragacanth, and gum acacia; dispersing or wetting agents, such as a naturally occurring phosphatide, e.g., lecithin, or condensation products of an alkylene oxide with fatty acids, for example of polyoxyethylene stearate, or a condensation products of ethylene oxide with long chain aliphatic alcohols, e.g., heptadecaethyleneoxycetanol, or condensation products of ethylene oxide with partial esters derived from fatty acids and a hexitol, e.g., polyoxyethylene sorbitol monooleate, or a condensation product of ethylene oxide with partial esters derived from fatty acids and hexitol anhydrides, e.g., polyoxyethylene sorbitan monooleate. The aqueous suspensions can also contain one or more preservatives, for example ethyl or n-propyl p-hydroxy benzoate, one or more coloring agents, one or more flavoring agents, and one or more sweetening agents, such as sucrose, saccharin, or sodium or calcium cyclamate.

Dispersable powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example, sweetening, flavoring, and coloring agents, can also be present.

Syrups and elixirs can be formulated with sweetening agents, such as glycerol, sorbitol or sucrose. Such formulations may also contain a demulcent, a preservative and flavoring and coloring agents.

The pharmaceutical compositions can be in the form of a sterile injectable preparation, for example, as a sterile injectable aqueous suspension. This suspension can be formulated according to the known art using those suitable dispersing or wetting agents and suspending agents which have been mentioned above. The sterile injectable preparation can also be a sterile injectable solution or suspension in a nontoxic parenterally-acceptable diluent or solvent, for example, as a solution in 1,3-butanediol.

In general, water, a suitable oil, saline, aqueous dextrose (glucose), polysorbate and related sugar solutions, emulsions, such as Intralipid® (Cutter Laboratories, Inc., Berkley Calif.) and glycols such as propylene glycol or polyethylene glycols are suitable carriers for parenteral solutions. Antioxidizing agents, such as but not limited to sodium bisulfite, sodium sulfite, or ascorbic acid, either alone or combined, are suitable stabilizing agents. Also used can be citric acid and its salts and sodium EDTA. In addition, parenteral solutions can contain preservatives, such as but not limited to benzalkonium chloride, methyl- or propylparaben, and chlorobutanol.

The pharmaceutical compositions of the present invention also include compositions for delivery across cutaneous or mucosal epithelia including transdermal, intranasal, sublingual, buccal, and rectal administration. Such compositions may be part of a transdermal device, patch, topical formulation, gel, etc., with appropriate excipients. Thus, the compounds of the present invention can be compounded with a penetration-enhancing agent such as 1-n-dodecylazacyclopentan-2-one or the other penetration-enhancing agents disclosed in U.S. Pat. Nos. 3,991,203 and 4,122,170 which are hereby incorporated by reference in their entirety to describe penetration-enhancing agents which can be included in the transdermal or intranasal compositions of this invention.

Suitable pharmaceutical carriers are described in *Remington's Pharmaceutical Sciences,* Mack Publishing Company, a standard reference text in this field, which is incorporated herein by reference in its entirety.

Various modifications of the invention in addition to those shown and described herein will be apparent to those skilled in the art from the foregoing description. Such modifications are also intended to fall within the scope of the appended claims.

The foregoing disclosure includes all the information deemed essential to enable those skilled in the art to practice the claimed invention. Because the cited patents or publications may provide further useful information these cited materials are hereby incorporated by reference in their entirety.

EXAMPLE 1

Synthesis of BuBuOMB

The synthesis of BuBuOMB was done as follows: To a solution of 4-butyramidobutyric acid (1.56 g, 9 mmol) in dry dimethylformamide (DMF) (6 mL), at room temperature under nitrogen, were added chloromethyl butyrate (1.26 g, 1 eq) and triethylamine (1.5 mL, 1.1 g, 1.2 eq). The reaction mixture was heated to 65° C. for 3 h whereby a large amount of precipitate formed and TLC ($CHCl_3$:MeOH 7:1, detection-vanillin) showed that most of the acid had reacted. The precipitate was filtered and washed with ethyl acetate. The filtrate was partitioned between water and ethyl acetate. The aqueous phase was extracted back with a small amount of ethyl acetate, and the combined organic phase was washed three times with water, three times with a 5% solution of $NaHCO_3$, and twice with brine, dried with $MgSO_4$ and evaporated to give the crude product as a yellowish semisolid (1.6 g, 65% yield) which was chromatographed on silica gel (60 g, ethyl acetate:hexane:isopropanol 8:8:1). The product was found in the second fraction. The pure product (1 g, 40% yield) was a colorless oil.

EXAMPLE 2

Synthesis of BuBOMB

BuBOMB has the following structure:

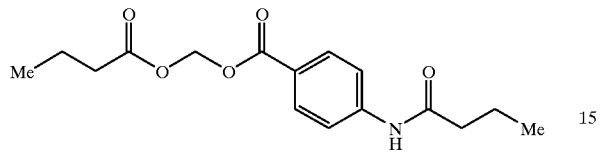

and was synthesized as follows. To a stirred solution of 4-butyramidobenzoic acid (3.33 g, 16.1 mmol) and chloromethyl butyrate (2.2 g, 1 eq) in dry DMF (10 mL), under nitrogen was dropwise added triethylamine (2.7 mL, 1.95 g, 1.2 eq). The reaction mixture was heated at 60° C. for 3 h, during that time a large amount of precipitate formed and TLC (ethyl acetate:hexane 1:1) showed that most of the acid has reacted. The precipitate was filtered and washed with ethyl acetate. The filtrate was partitioned between water and ethyl acetate. The aqueous phase was washed with a small amount of ethyl acetate, and the combined organic phase was washed with water (3×), 5% solution of $NaHCO_3$ (2×), brine (2×), dried with $MgSO_4$ and evaporated to give the crude product as a solid (3.3 g), which was crystallized from ethyl acetate-hexane to give a white solid (2.54 g, 77% yield), mp 89–90° C.

EXAMPLE 3

Synthesis of AmBOMB

AmBOMB has the following structure:

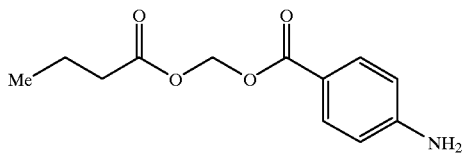

and was synthesized as follows. To a stirred solution of chloromethyl butyrate (21.5 g, 157 mmol) in DMF (60 mL), under nitrogen, 4-aminobenzoic acid (21.05 g, 153 mmol), was added, followed by the dropwise addition of triethylamine (25.5 mL, 18.5 g, 1.2 eq) until the acid dissolved. The reaction mixture was heated at 60° C. overnight, during that time a large amount of precipitate formed and TLC (ethyl acetate:hexane 2:1) showed that most of the acid has reacted. The precipitate was filtered and washed with ethyl acetate. The solution was partitioned between water and ethyl acetate. The aqueous phase was extracted with a small amount of ethyl acetate, and the combined organic phase was washed with a 5% solution of $NaHCO_3$ (3×) The organic phase was washed with water (2×), brine (2×) and dried with $MgSO_4$. Evaporation of the solvent gave a pasty residue which was triturated with hexane to give the product as white solid (18 g) and was crystallized from isopropanol. The first crop gave 6.7 g of white product. A second crop, obtained by concentrating the mother liquor gave an additional 3 g of material of the same quality. Additional crops of non-crystalline powdery material (5 g) were obtained by triturating, in a small amount of isopropanol, the residues upon evaporation of the mother liquors. The total purified product obtained was 15 g (41% yield), mp 130–132° C.

EXAMPLE 4

Synthesis of POMB

POMB has the following structure:

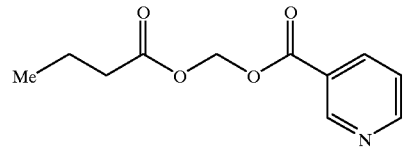

and was synthesized as follows. To a stirred solution of chloromethyl butyrate (26 g, 190 mmol) dissolved in DMF (90 mL), under nitrogen, nicotinic acid (23.4 g, 190 mmol), was added, followed by the dropwise addition of triethylamine (32 mL, 23.23 g, 1.2 eq) until the acid dissolved. The reaction mixture was heated at 60° C. overnight, during that time a large amount of precipitate formed and TLC (ethyl acetate:hexane 2:1) showed that most of the acid was consumed. The precipitate was filtered and washed with ethyl acetate (300 mL). The solution was washed with water (4×), the aqueous phase was extracted with a small amount of ethyl acetate (3×10 mL) and the combined organic phase was washed with brine (2×), dried over $MgSO_4$ and evaporated. The product was obtained as a brownish oil (31.7 g), which was distilled at 109–110° C. (0.05 mm Hg) to give a colorless liquid (25 g, 59% yield).

EXAMPLE 5

Synthesis of MePOMB•I and Additional Compounds

MePOMB•I, the iodide salt of MePOMB, was synthesized by adding methyliodide (MeI) (1.55 mL, 3.55 g, 25 mmol) to a solution of 3-pyridoyloxymethyl butyrate (975 mg, 4.4 mmol) in dry acetone (100 mL). The reaction mixture was refluxed for 20 h and a fine precipitate was formed which was filtered and washed with acetone. The filtrate was evaporated to give the product, MePOMB•I. The chloride salt can be made, for example, by stirring MEPOMB•I with silver chloride in an inert solvent such as acetone, followed by the removal of the silver iodide.

Additional compounds of the invention are provided in Table I. These compounds are those of Formula I or Ia having the designated groups. These compounds can be synthesized in a manner analogous to Examples 1–5 or as provided in the Detailed Description of the Invention.

TABLE 1

Additional Compounds

| R | R¹ | R² | R³ |
|---|----|----|----|
| $CH_2=CHCH_2-$ | H | H | 4-pyridyl |
| $ClCH_2CH_2CH_2-$ | $CH_3$ | H | 2-methyl-6-(NHCH$_3$)phenyl |
| $CH_3CH_2CH(CF_3)CH_2-$ | $CH_3$ | $CH_3$ | $-CH_2CH_2-$(N-methyl-tetrahydropyridyl) |
| $C_6H_5(CH_2)_3-$ | $C_3H_7$ | H | [N-methylpyridinium]$^+$ Br$^-$ |
| 2-pyridyl-$CH_2$- | H | H | $-CH_2CH_2CH_2N(CH_3)_2$ |
| 4-$CH_3O$-phenyl-$CH_2-$ | $C_3H_7$ | H | $-CH_2-$(6-methyl-2-pyridyl) |

EXAMPLE 6

Clonogenicity of Established Tumor Cell Lines

Inhibition of tumor growth was tested using cell lines as follows:

The cell lines listed in Table 2 were grown to 70–80% confluence in complete media [RPMI 1640 containing 10% FCS, 100 IU penicillin, 100 μg/mL streptomycin and 2 mM L-glutamine]. Cells were harvested, washed in complete media, and counted. Cell viability was determined by trypan blue exclusion. The cells were placed into soft agar (0.12% in media) and plated at 5,000 viable cells per well onto an agarose underlayer (0.4%) in 24-well plates. After overnight culture, AB, POMB or AmBOMB was added at the indicated concentration. Control cells received media alone. As a control for cell death, cells were treated with a superlethal dose of 10 μg/ml of cisplatin. The dosage of AB, POMB or AmBOMB which inhibited fifty percent (or ninety percent) of cell proliferation ($IC_{50}$ or $IC_{90}$) was calculated using the Chou Analysis' Median Effective Dose equation.

Clonogenicity is determined as the percentage of clones in treated cultures relative to clones in media-treated control cultures. A representative clonogenicity titration curve for AB, POMB and AmBOMB is shown with four neuroblastoma cell lines in FIG. 1. The $IC_{50}$ and $IC_{90}$ values of AB, POMB and AmBOMB for cancer cell lines are provided in Table 3.

The results demonstrate that POMB and AmBOMB are more potent growth inhibitors than AB. The data show that POMB, AmBOMB and AB inhibit cell proliferation in a dose-dependent manner but that the cells are at least an order of magnitude more sensitive to POMB and AmBOMB. The ratio of $IC_{50}$ AB:$IC_{50}$ AmBOMB ranges between 6- to 56-fold with a median of 21 μM and the ratio of $IC_{50}$ AB:$IC_{50}$ POMB ranges between 3.7- to 81-fold with a median of 21 μM. Similarly the ratio of $IC_{90}$ AB:$IC_{90}$ AmBOMB ranges between 14- to 791-fold with a median value of 45 μM and the ratio of $IC_{90}$ AB:$IC_{90}$ POMB ranges between 16- to 277-fold with a median value of 47 μM. The $IC_{90}$ values are clinically important for assessing eradication of residual cancer disease.

TABLE 2

Human Tumor Cell Lines

| Cell Lines | Origin |
|---|---|
| MCF7-WT | Breast Carcinoma |
| MCF7-40F | Breast Carcinoma |
| PC3 | Prostate Carcinoma |
| LNCaP | Prostate Carcinoma |
| K-562 | Erythroleukemia |
| SK-N-SH | Neuroblastoma |
| NBAS-5 | Neuroblastoma |
| IMR-32 | Neuroblastoma |
| LA1-5S | Neuroblastoma |
| NBL-W-N | Neuroblastoma |
| SMS-KAN | Neuroblastoma |
| SK-N-MC | Neuroblastoma |
| NGP | Neuroblastoma |
| SMS-KCN | Neuroblastoma |

TABLE 3

Inhibition of Established and Primary Tumor
Cell Lines by AB, AmBOMB and POMB

| Cell Line | AB IC$_{50}$[a] | AB IC$_{90}$ | AmBOMB IC$_{50}$ | AmBOMB IC$_{90}$ | Ratio AB/AmBOMB IC$_{50}$ | Ratio AB/AmBOMB IC$_{90}$ | POMB IC$_{50}$ | POMB IC$_{90}$ | Ratio AB/POMB IC$_{50}$ | Ratio AB/POMB IC$_{90}$ |
|---|---|---|---|---|---|---|---|---|---|---|
| MCF7-WT | 1500 | 9473 | 42 | 112 | 35.7 | 84.6 | 44 | 84 | 34.1 | 112.8 |
| MCF7-40F | 817 | 3183 | 40 | 83 | 20.4 | 38.3 | 51 | 195 | 16 | 16.3 |
| PC3 | 226 | 4478 | 23 | 188 | 9.8 | 23.8 | 61 | 186 | 3.7 | 24.1 |
| LNCaP | 780 | 6703 | 35 | 90 | 22.3 | 74.5 | 53 | 143 | 14.7 | 46.9 |
| K562 | 772 | 6658 | 43 | 156 | 18 | 42.7 | 57 | 141 | 13.5 | 47.2 |
| SK-N-SH | 998 | 3397 | 40 | 62 | 25 | 54.8 | 31 | 99 | 32.2 | 34.3 |
| NBAS-5 | 883 | 13030 | 21 | 44 | 42 | 296.1 | 20 | 47 | 44.2 | 277.2 |
| SK-N-MC | 215 | 1314 | 26 | 91 | 8.3 | 14.4 | 11 | 25 | 19.5 | 52.6 |
| IMR-32 | 881 | 3566 | 21 | 46 | 42 | 77.5 | 27 | 69 | 32.6 | 51.7 |
| NGP | 197 | 1622 | 33 | 83 | 6 | 19.5 | 15 | 40 | 13.1 | 40.6 |
| LA1-5S | 1627 | 2675 | 29 | 59 | 56.1 | 45.3 | 20 | 33 | 81.4 | 81.1 |
| SMS-KCN | 1872 | NA | 89 | NA | 21 | NA | 99 | 739 | 18.9 | NA |
| NBL-W-N | 489 | 3074 | 47 | 154 | 10.4 | 20 | 22 | 47 | 22.2 | 65.4 |
| SMS-KAN | 1138 | 2079 | 49 | 152 | 23.2 | 791.6 | 26 | 57 | 43.8 | 36.5 |
| Primary[b] | 464 | 2120 | 32 | 57 | 13.5 | 37 | 41 | 97 | 11 | 22 |

[a]All concentrations are in $\mu$M.
[b]Data from 53 primary tumor cell lines treated as described in Example 3.

EXAMPLE 7

Inhibition of Clonogenicity of Primary Tumor Cells

The effect of AmBOMB and POMB was compared to that of AB on a variety of primary tumor cells as described in Example 2, except that cells were seeded at 30,000 cells per well. Table 3 provides the average IC$_{50}$ value and IC$_{90}$ value for each compound as well as the IC$_{50}$ and IC$_{90}$ ratio of each compound to AB. The tested tumor cells were from 11 non-small cell lung carcinomas, 10 breast carcinomas, 10 gastric carcinomas, 10 ovarian carcinomas, and 10 CNS tumors. The results demonstrate that AmBOMB and POMB are more potent inhibitors of cell proliferation than is AB, especially for lung, breast, ovarian, CNS and gastrointestinal cancers.

EXAMPLE 8

Inhibition of Cancer Cell Proliferation Assessed by the SRB Assay

Figure 2A:
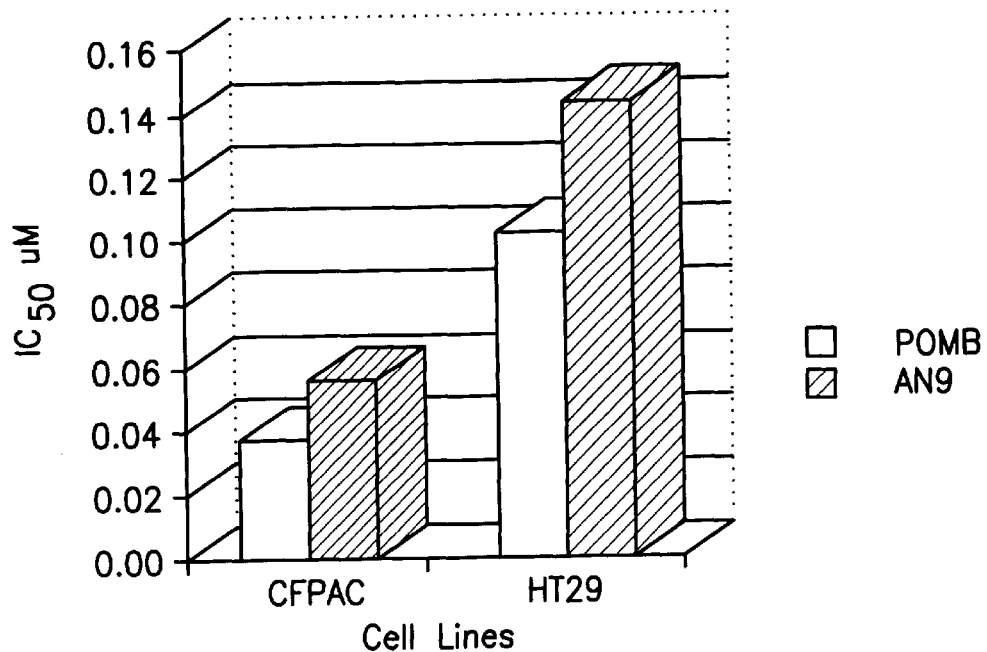
FIG. 2 is a bar graph comparing the $IC_{50}$ and $IC_{90}$ values of POMB or AN-9 on the cell lines CFPAC and HT29 as assessed in the SRB assay.
Figure 2B:
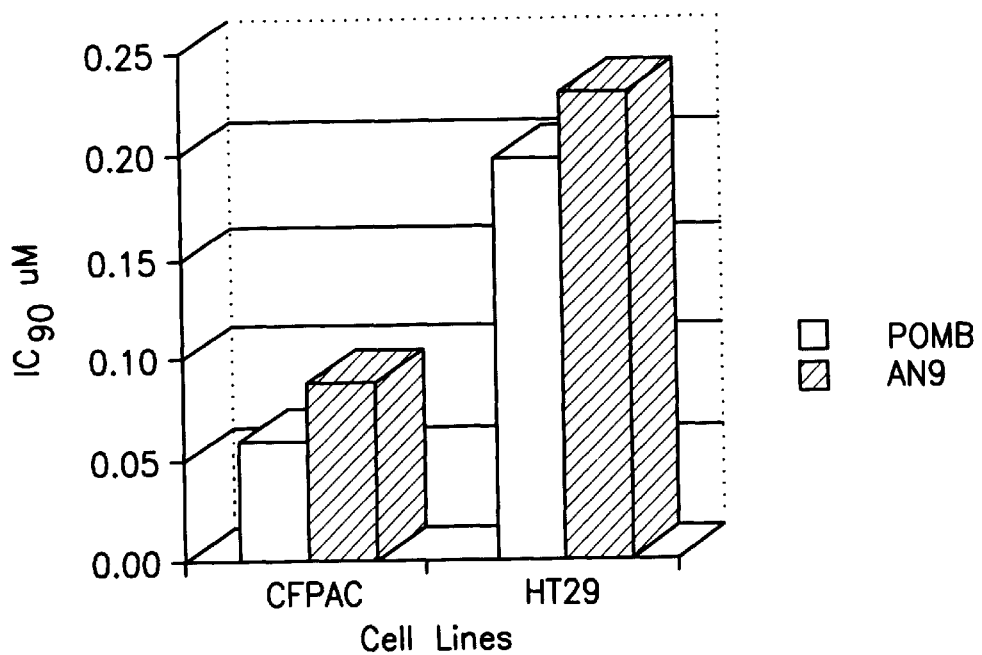

The inhibition of cell proliferation was measured in the indicated cancer cell lines using the sulforhodamine B (SRB) assay as described by Monks et al., 1991, *J. Natl. Can. Inst.* 83:757–766. The SRB assay is used to screen for anti-cancer drugs. A comparison of POMB, AB and AN-9 demonstrates that POMB exerts at least 100-fold greater activity than AB as measured by the IC$_{50}$ and IC$_9$ values (Table 4). POMB was also 1.2- to 1.5-fold more active than AN-9 as determined by the IC$_{50}$ and IC$_{90}$ values. (Table 4 and FIG. 2).

TABLE 4

Comparison of POMB, AB and AN-9 in the SRB Assay

| AGENT | CFPAC IC$_{50}$ * | CFPAC IC$_{90}$ * | HT29 IC$_{50}$ | HT29 IC$_{90}$ |
|---|---|---|---|---|
| AB | >4.000 | >4.000 | >4.000 | >4.000 |
| POMB | 0.037 | 0.0604 | 0.103 | 0.198 |
| AB/POMB | 108 | 66.22 | 39 | 20.250 |

TABLE 4-continued

Comparison of POMB, AB and AN-9 in the SRB Assay

| AGENT | CFPAC IC$_{50}$ * | CFPAC IC$_{90}$ * | HT29 IC$_{50}$ | HT29 IC$_{90}$ |
|---|---|---|---|---|
| AN9 | 0.0559 | 0.0898 | 0.144 | 0.231 |
| AN9/POMB | 1.51 | 1.48 | 1.4 | 1.160 |

EXAMPLE 9

Effect POMB and AN-9 on Hyperproliferating Cells

Figure 3:
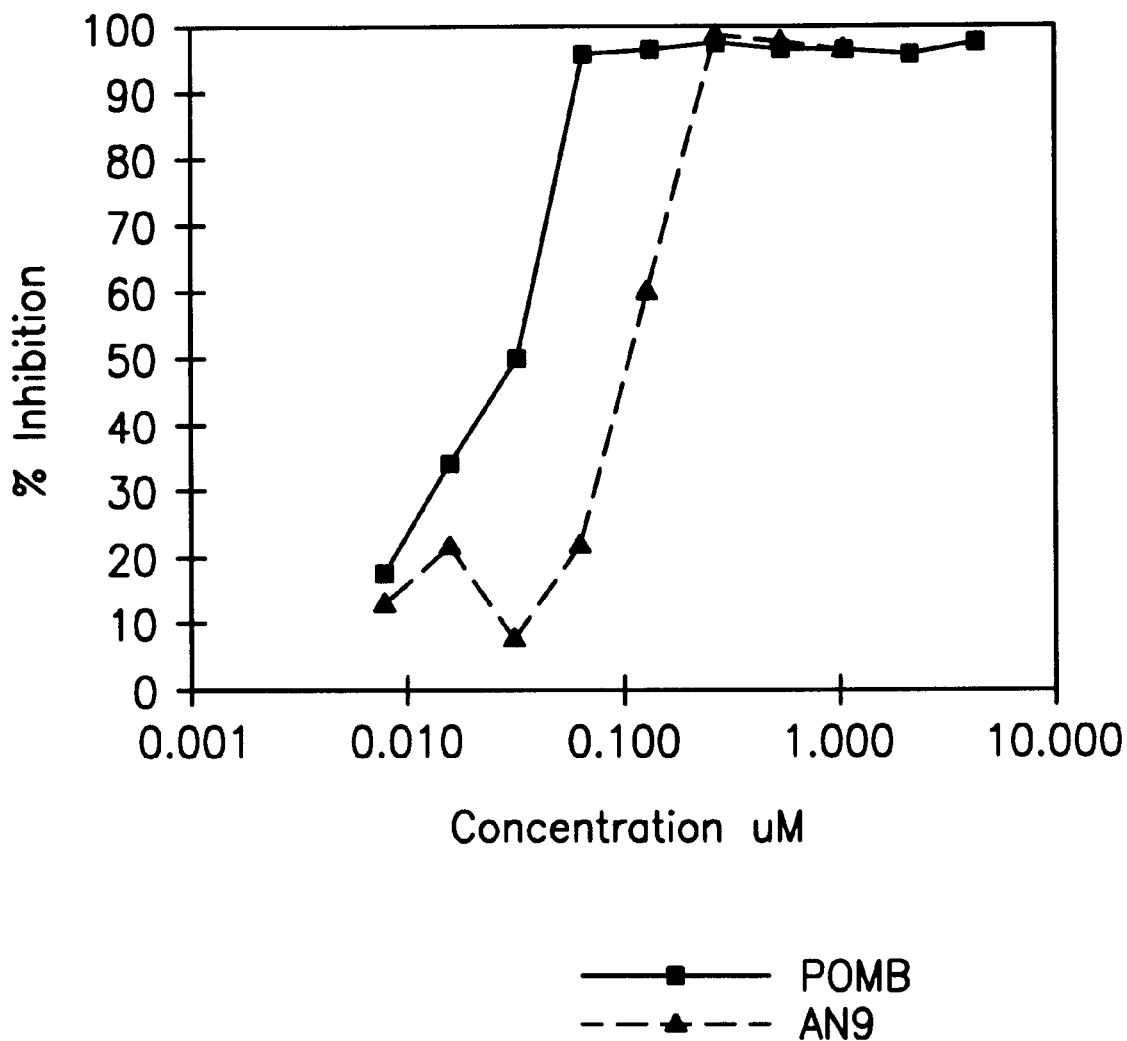
FIG. 3 is a graphic illustration showing the in vitro inhibition of cellular growth by POMB and AN9 on immortalized human keratinocytes as a function of concentration (in $\mu M$).

The SRB assay was used to compare the effect of POMB and AN-9 on the proliferation of hyperproliferating, immortalized human keratinocytes as described in Example 8 (FIG. 3). The IC$_{50}$ and IC$_{90}$ of POMB on the keratinocytes was 0.032 and 0.058, respectively, whereas for AN-9 the same parameters were 0.108 and 0.221, respectively.

EXAMPLE 10

Clonogenicity of Human Pancreatic Cells

The effect of 24 h exposure to POMB, AMBOMB, BUBOMB, and AB was determined by a colony-forming assay on the pancreatic cell line BxPC-3, a primary adenocarcinoma ACTTnr:CRL-1687. Freshly trypsinized cells were plated at 500 cells/dish in 60 mm$^2$ tissue culture dishes with the indicated concentration of each compound and incubated for 24 h at 37° C. in 5% CO$_2$/air atmosphere. The cultures were washed with PBS, fresh medium was added, and the cultures were incubated for 7–12 days to allow the formation of colonies. Colonies were fixed with methanol, stained with Giemsa and counted. All incubations were performed in triplicate.

Figure 4:
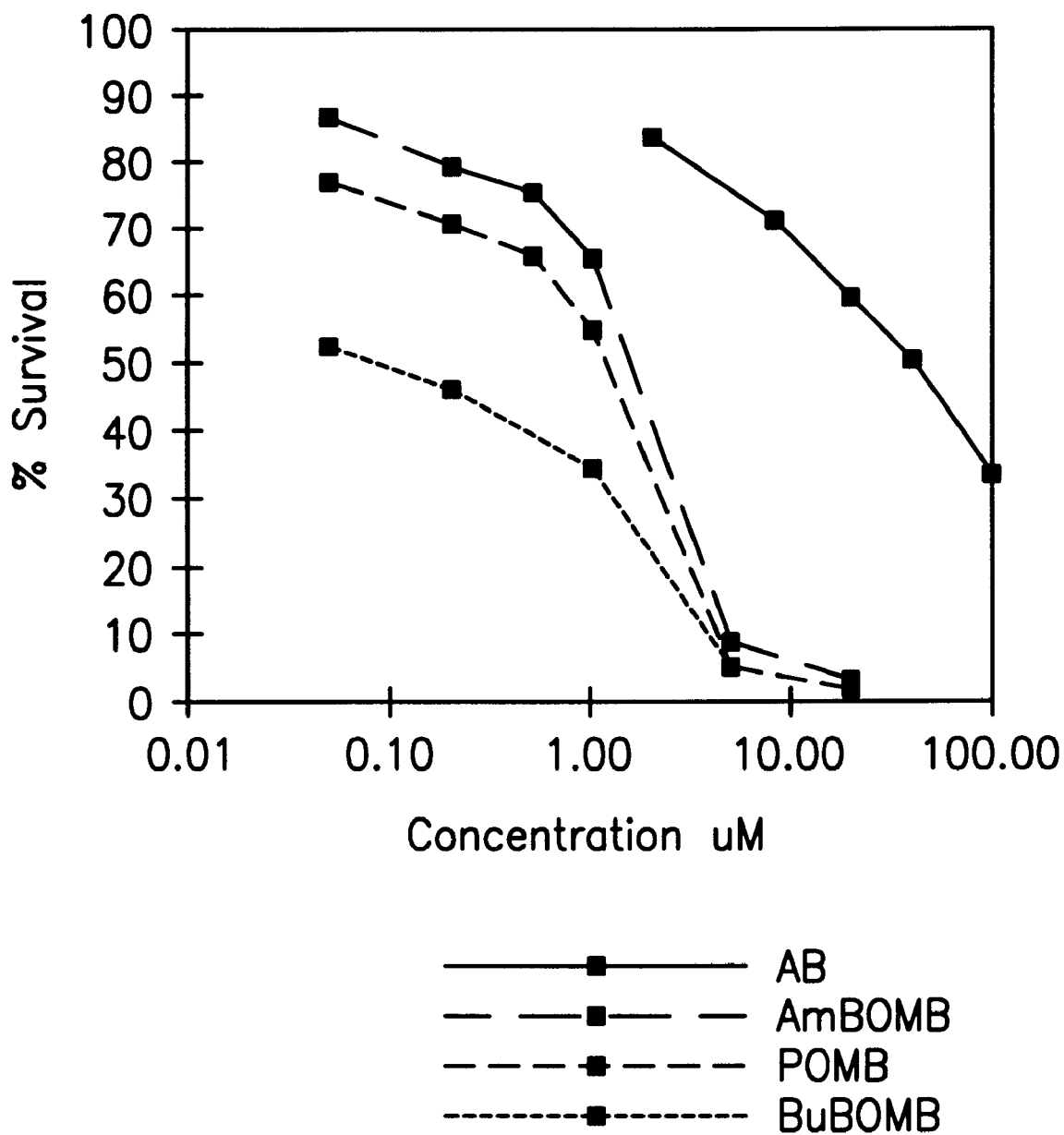
FIG. 4 is a graphic illustration showing the in vitro inhibition of cellular growth by AB, AmBOMB, POMB or BuBOMB on a primary human pancreatic adenocarcinoma cell line (BxPC-3) as a function of concentration (in $\mu M$).

The results shown in FIG. 4 demonstrate that 24 h treatment with POMB, AmBOMB and BuBOMB caused a dose-dependent growth inhibition, with complete inhibition occurring at concentrations above 50 $\mu$M. In contrast, a 100 $\mu$M dose of AB did not cause complete growth inhibition of the cells.

EXAMPLE 11

Synergy of AB and AmBOMB with Antiviral Agent

Figure 5A:
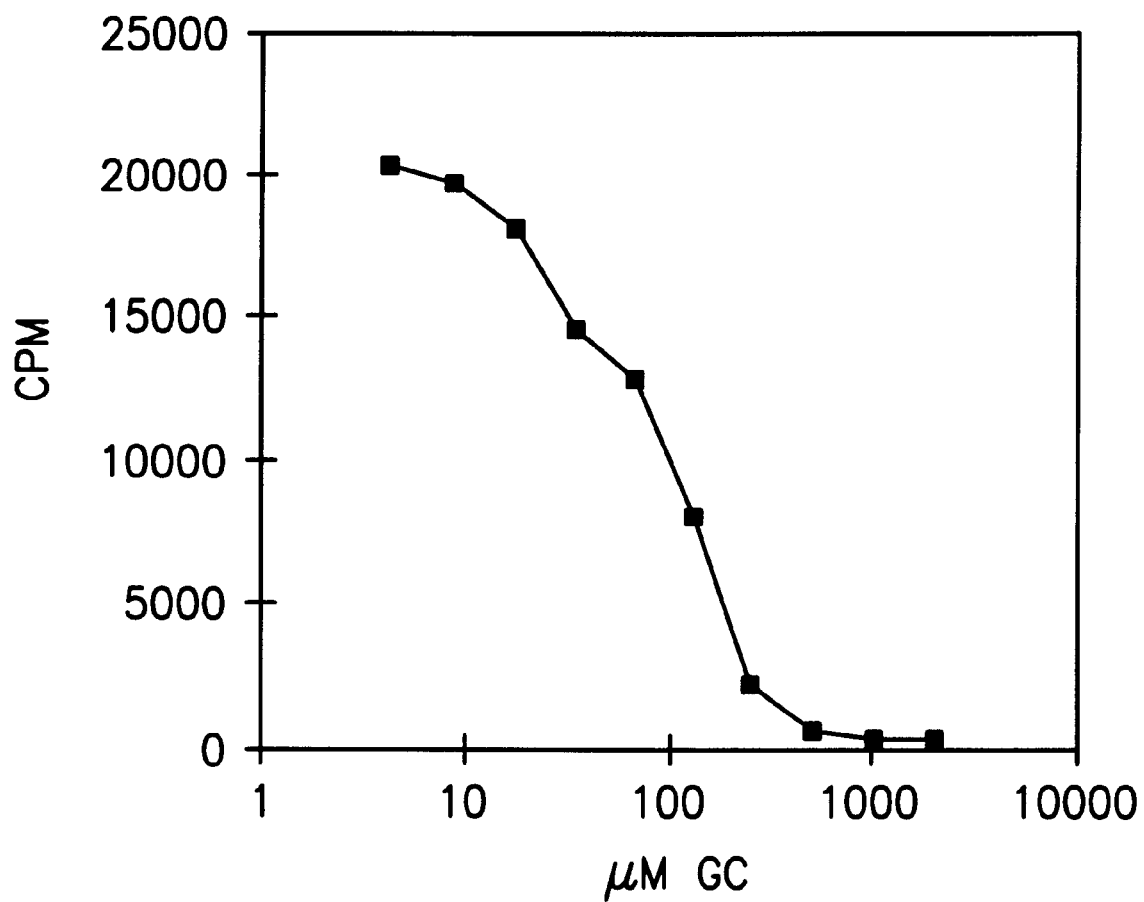
FIG. 5 is a graphic illustration showing growth inhibition measured by reduction of [$^3$H]-thymidine uptake in an EBV-transformed cell line as a function of concentration of ganciclovir (GC) (panel A), GC and AB (panel B) and GC and AmBOMB (panel C). In panels B and C, the GC concentration is indicated in the inset. Concentrations are in $\mu M$.
Figure 5B:
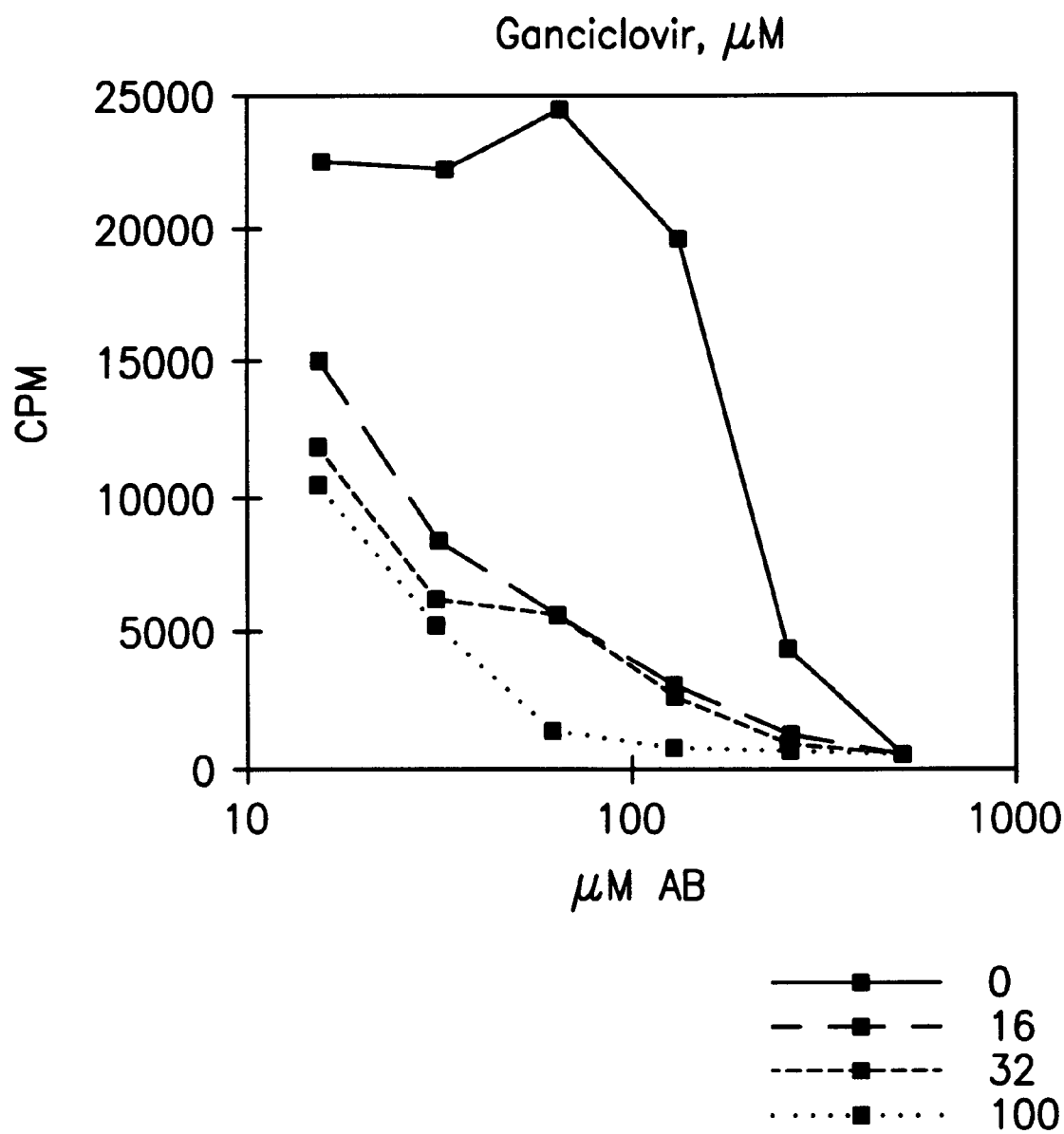
Figure 5C:
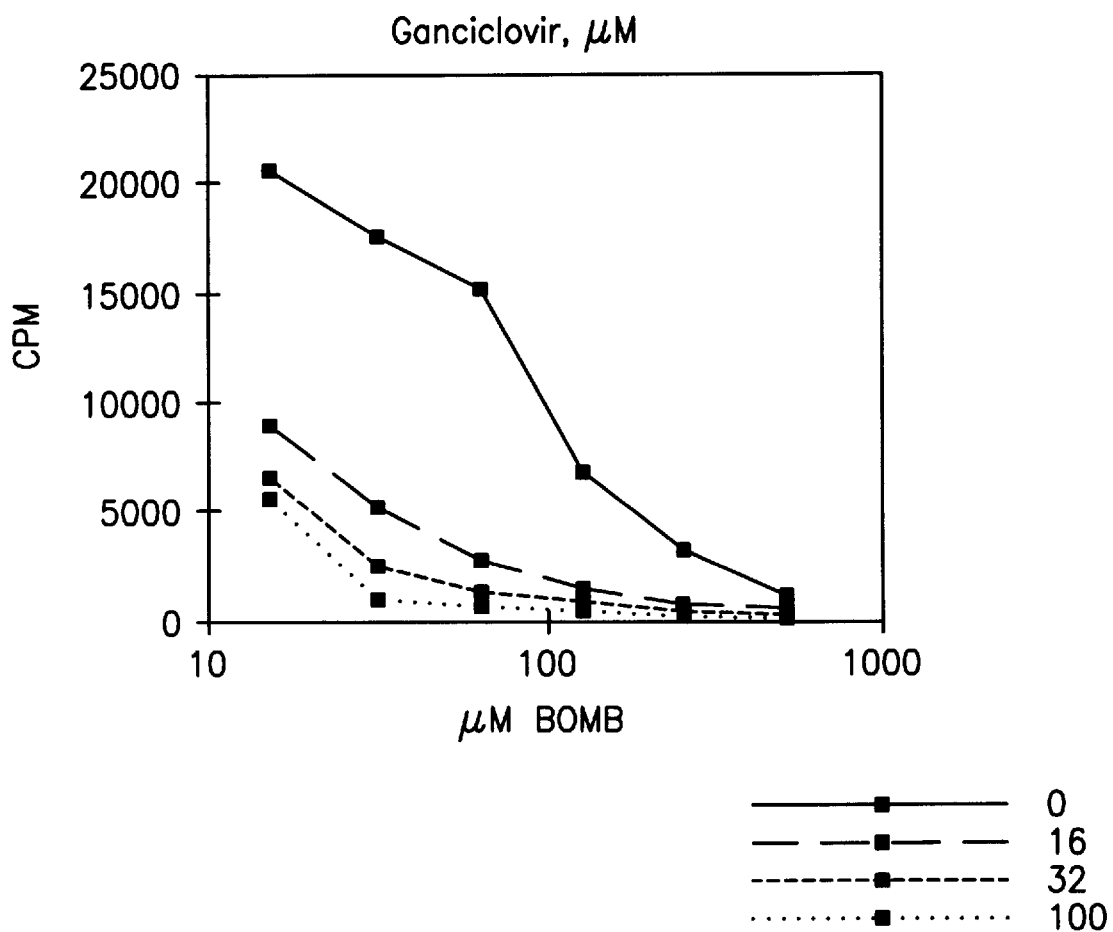

The effect of AmBOMB to AB was compared on EBV virus-associated tumors. EBV-positive cells from P3HR-1, a human lymphoma cell line, were incubated in growth medium with the specified concentration of AmBOMB, AB, ganciclovir (GC), or combination of these, for 72 hours, seeded in 96-well plates and pulsed with 1 $\mu$Ci [$^3$H]-thymidine/well during the last 16 hours of exposure to the compounds. Cells were harvested with a cell harvester, using glass microfiber filters. The incorporation of [$^3$H]-thymidine was determined by retention of the acid insoluble fraction on filters and is expressed as CPM. The results of a representative experiment are shown in FIG. 5. FIG. 5A shows a titration curve using GC; FIG. 5B shows titration curves using GC and AB; and FIG. 5C shows similar titration curves for GC and AmBOMB; the GC concentration is indicated in the inset of panels B and C.

The results show that AmBOMB is about as potent as AB in inhibiting EBV-positive lymphoma cells, but importantly, that AB and AmBOMB interact synergistically with GC to inhibit proliferation of an EBV-associated tumor cell line.

EXAMPLE 12

Inducing Differentiation

Cancer cell differentiation was evaluated in a human leukemia cell line by nitroblue tetrazolium reduction (NBT) activity (Koeffler, *Blood*, 62: 709–721, 1983) or by changes in expression of inyelocytic maturation marker CD11b. Differentiation was also evaluted in a breast carcinoma cell line by lipid staining (Bacus et al., *Mol. Carcinog.* 3:350–362, 1990).

Figure 6A:
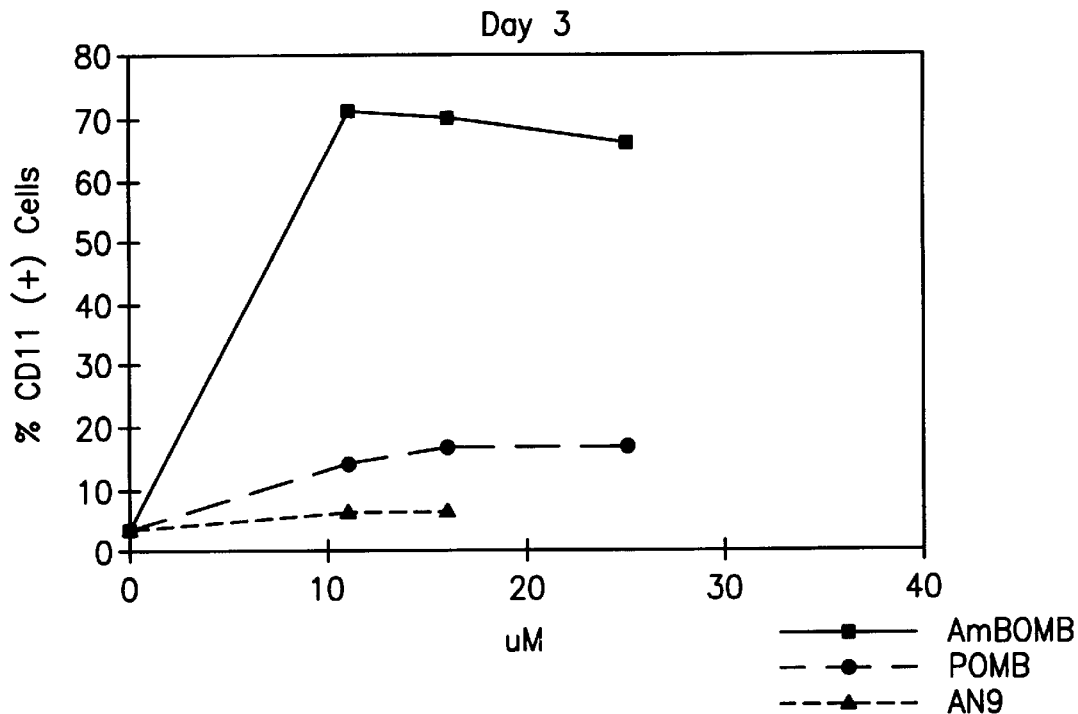
FIG. 6 is a graphic illustration showing the percentage of human leukemic cells (HL-60) expressing the phenotypic differentiation marker CD11b for cells which had been treated with AmBOMB, POMB or AN9 for 3 days (top panel) or 6 days (bottom panel). Concentrations are in $\mu M$.
Figure 6B:
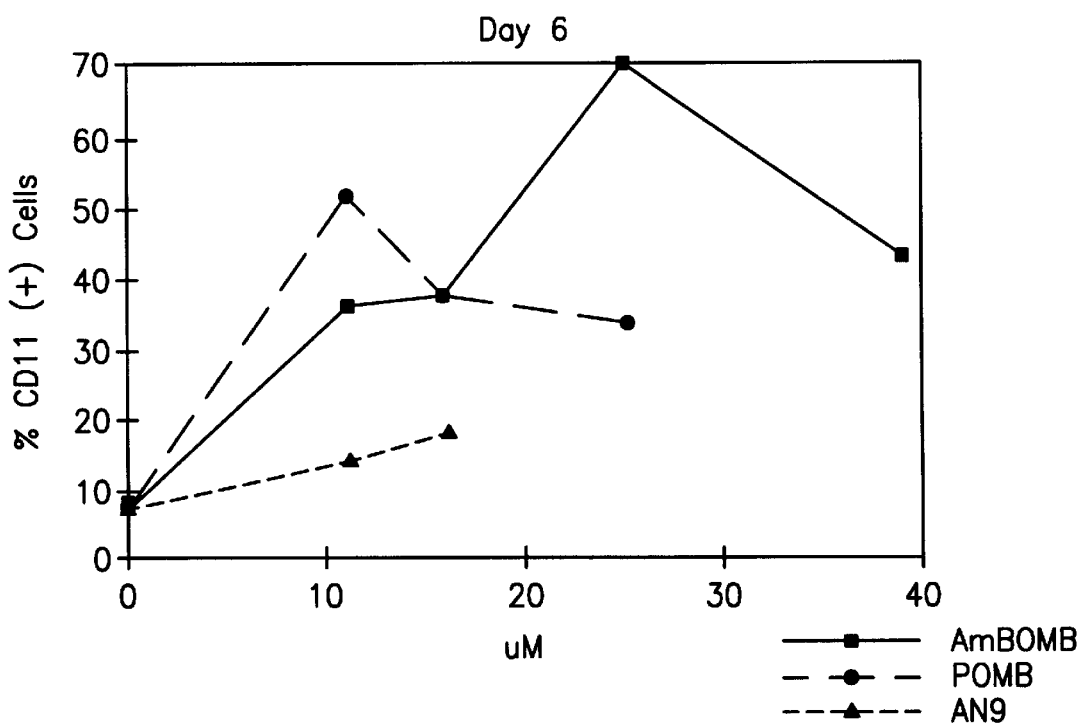

The level of CD11b was measured on HL-60 cells by flow cytometry using a monoclonal antibody (MAb) against CD11b in a standard indirect immunofluorescence assay. Cells were cultured for 3 or 6 days with the indicated concentration of AmBOMB, POMB or AN-9. Cultured cells were collected by centrifugation, resuspended at 10$^6$ cells per 20$\mu$ RPMI+10% FCS and incubated with MAb for 30 min at 40° C. The cells were washed twice in cold PBS+10% FCS and incubated with a 1:20 dilution of FITC-conjugated F(ab')$^2$ fragment of rabbit anti-mouse IgG for 20–30 min at 40° C. in the dark. After washing the cells twice in cold PBS+10% FCS, the flow cytometry was performed. The results are shown in FIG. 6. AmBOMB was the most active differentiation inducer and AN-9 was the least active.

Figure 7:
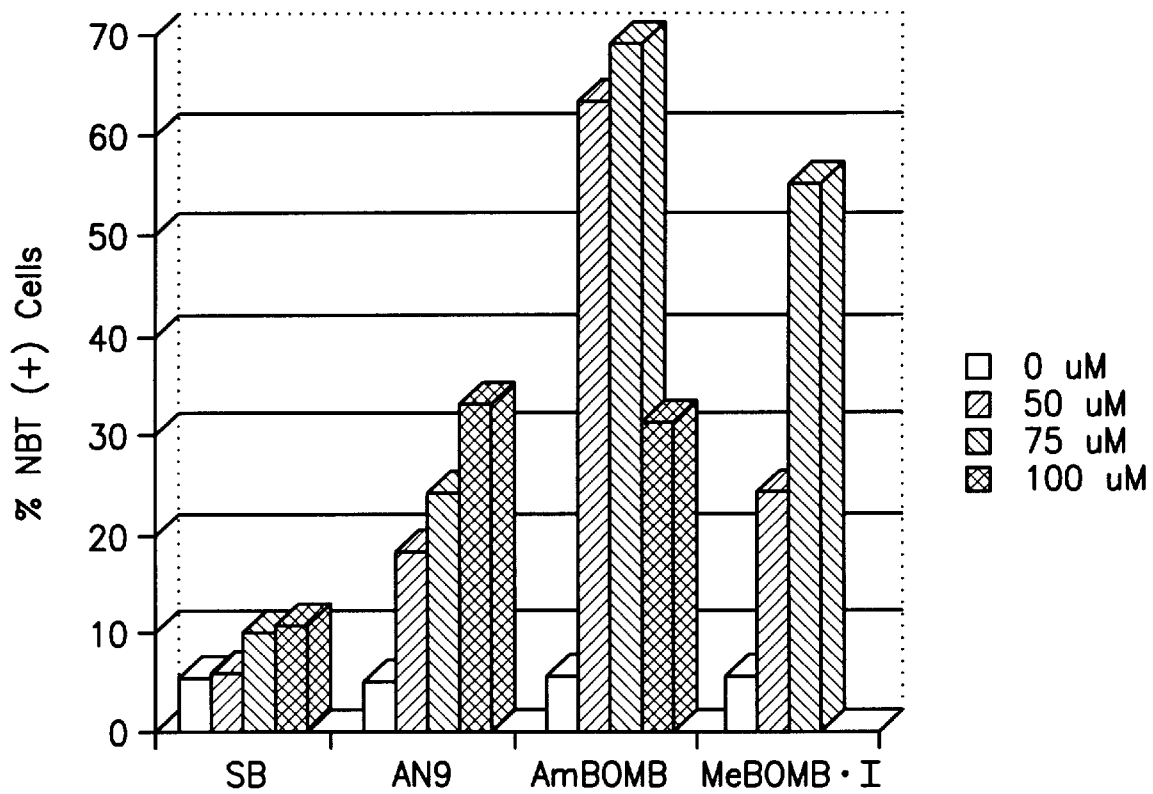
FIG. 7 is a bar graph showing the percentage of NBT-positive HL-60 cells for cells which had been treated with SB, AN9, AmBOMB or MePOMB•I. Concentrations are in $\mu M$.

The differentiation ability of AmBOMB and MePOMB•I with the human leukemia cell line HL-60 was compared to AN-9 and SB. Briefly, HL-60 cells were incubated with the indicated concentration of compound for three days, washed, resuspended in saline containing 0.1% NBT and stimulated with 0.4 $\mu$M phorbol ester for 30 minutes at 37° C. The cells were examined microscopically and at least 200 cells were scored. The results are provided graphically in FIG. 7 and demonstrate that AmBOMB and MePOMB•I are substantially more active at inducing differentiation than SB. In general AmBOMB and MePOMB•I are much more active than AN-9 at comparable concentrations.

In the case of the human breast carcinoma cell line Au565, 100% of the cells treated with 10 $\mu$M POMB were positive for lipid staining whereas less than 1% of cells treated with the same concentration of AB were positive for lipid staining. In MCF-7 cells, another breast carcinoma cell line, 50% of the cells were positive for lipid staining at 50 $\mu$M, a concentration at which AB did not induce differentiation.

EXAMPLE 13

Induction of Apoptosis

Apoptosis was measured as described by Telford et al., 1991, *Cell Physiol.* 24:447–459, in HL-60 cells and in the human erthroblastic cell line, K-562. Cells were treated with AmBOMB•HCl or POMB for 3 days, fixed, stained with propidium iodine and analyzed by flow cytometry for cell cycle distribution. A distinct subpopulation of cells was observed in a region below the G0–G1 cells. This region consisted of cells with fragmented DNA. The increase in apoptotic cells in HL-60 and K-562 cells lines treated with varying concentrations of AmBOMB•HCl or POMB is shown in Table 4.

Induction of apoptosis by POMB and AB in MCF-7 cells was evaluated by staining cells with the WAF antibody and by Western blot analysis as described by Bacus et al., 1996, *Oncogene* 12:2535–2547. The percentage of cells expressing WAF was 14% in the controls. The results demonstrate that POMB induces apoptosis in a dose-dependent manner and that POMB induces apoptosis at a 10-fold lower concentration and to a greater extent than does AB (Table 5).

TABLE 4

Induction of Apoptosis in Human Leukemia Cell Lines

| Compound | Concentration ($\mu$M) | % Apoptotic Cells HL-60 | % Apoptotic Cells K562 |
| --- | --- | --- | --- |
| AmBOMB.HCl | 55 | 10.5 | 11.2 |
|  | 110 | 20.6 | 15 |
|  | 165 | 76 | 20.3 |
| POMB | 12.5 | 12.4 | 9.7 |
|  | 25 | 80 | 73 |
|  | 37.5 | 79 | 82 |

TABLE 5

Apoptosis in Human Breast Cancer Cells

| Concentration ($\mu$M) | AB* | POMB* |
| --- | --- | --- |
| 10 | ND** | 21 |
| 25 | ND | 19 |
| 50 | ND | 59 |
| 100 | 23 | 56 |

*Percentage of cells expressing the WAF protein.
**ND, not detected.

EXAMPLE 14

Induction of Hemoglobin Synthesis

Hb Measurement: Hemoglobin (Hb) was measured by benzidine staining of K562 cells after 5 days exposure to AmBOMB, POMB, BuBOMB or AB according to the procedure of Fibach et al. (1993), infra. Quantitative measurement of HbF in K562 culture or human erythroid cultures was determined by ion-exchange high pressure liquid chromatography (HPLC) as described by Fibach et al., *Blood* 81:1630–1635, 1993.

K562 cells: K562 is an erthroblast cell line that develops some properties of erythroid, megakaryocyte or monocyte cells, depending on the specific stimulus, when induced by different chemicals. K562 cells were grown in RPMI with 10% FCS, supplemented with 2 mM glutamine. Cells were incubated at 37° C. in a humidified, 5% $CO_2$ incubator.

Treatment of K562 cells with AmBOMB, POMB, BuBOMB or AB showed that, on a molar basis, the three compounds of the invention had higher activity in inducing erythroid differentiation (hemoglobin accumulation) than did AB. This was evident from the higher proportion of Hb-containing cells per the total cell population (Table 6) as well as the total Hb content of the cultures (Table 7). The extent of differentiation of the treated cultures was directly related to the drug dose. The diluents, DMF and water, had no effect on cell growth, cell viability or differentiation.

Erythroid cells: Erythroid cells were isolated from peripheral blood of healthy individuals by the method of Fibach (1993). The results showed that BuBOMB, POMB and BuBuOMB increased HbF in cultured erythroid cells relative to untreated control cultures (Table 8).

TABLE 6

Percentage K562 Cells Containing HbF

| Concentration ($\mu$M) | AB | AmBOMB | POMB | BuBOMB |
|---|---|---|---|---|
| 10 | ND** | 17 | 5.3 | 4.7 |
| 50 | 3 ± 2 | — | 13 | 11 |
| 100 | ND | — | 24.7 | 22.3 |

**ND, not detected

TABLE 7

HbF Synthesis in K562 Cells

| Concentration ($\mu$M) | AB* | AmBOMB* | POMB* | BuBOMB* |
|---|---|---|---|---|
| 10 | 0.96 | 15 | 15 | 27.5 |
| 50 | 0.95 | 24 | 37 | 30.5 |
| 100 | 1.8 | — | 39 | 11.5 |

*HbF in $\mu$g/mL.

TABLE 8

Percentage Erythroid Cells Containing HbF

| Treatment | Concentration ($\mu$M) | % HbF | % Increase |
|---|---|---|---|
| Untreated |  | 2.08 |  |
| BuBOMB | 100 | 2.55 | 122 |
|  | 200 | 4.93 | 237 |
| POMB | 100 | 2.7 | 129 |
|  | 200 | 2.36 | 113 |
| BuBuOMB | 100 | 2.52 | 121 |
|  | 200 | 2.83 | 136 |

EXAMPLE 15

Altering HER-2/neu and ICAM Gene Expression

Increased expression of HER-2/neu is associated with poor prognosis in breast cancer patients so that reducing expression of this gene can be beneficial to cancer patients. In contrast, increased expression of the extracellular matrix protein ICAM-1 is associated with maturation, i.e., differentiation, of AU565 cancer cells so that increasing ICAM expression can be beneficial to cancer patients.

The relative levels of expression of these two genes was measured by fixing and using immunocytostaining with a monoclonal antibody (MAb) to measure the quantities of each gene product. The cultured cells were AU565, a breast carcinoma cell line, grown in the presence of POMB or AB. The primary MAb was ICAM-1 specific and the primary MAb for detecting HER-2/neu was N24 (from the Weizmann Institute). Cells were also counterstained for DNA content using a modified Feulgen method. Antibody binding was determined using an alkaline phosphatase chromogen in a biotin-streptavidin sandwich assay and quantitated by image analysis. The basal expression level of each gene was determined on AU565 cells grown at low density, in the absence of POMB or AB and was arbitrarily set at 1.0 to determine relative expression levels.

The results shown in Table 9 demonstrate that POMB inhibits the expression of the oncogene HER-2/neu and induces increased expression of the ICAM gene product relative to AB.

TABLE 9

Expression of HER-2/Neu and ICAM

|  | HER-2/Neu | ICAM |
|---|---|---|
| Control | 1.0 | 0 |
| POMB | 0.36 | 1.2 |
| AB | 1 | 0 |

* Relative concentrations

We claim:
1. A compound represented by the formula:

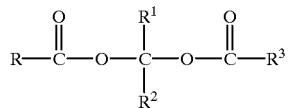

wherein
R is $C_3$ to $C_6$ alkyl, alkenyl or alkynyl, any of which can be optionally substituted with aryl, heteroaryl, halo, alkyl, alkoxy, hydroxy, amino, cyano, nitro, trifluoromethyl, acylamino or carbamoyl;

$R^1$ and $R^2$ are independently H, $C_1$–$C_{10}$ alkyl, $C_2$–$C_{10}$ alkenyl, or $C_2$–$C_{10}$ alkynyl, any of which can be optionally substituted with halo, alkoxy, amino, trifluoromethyl, aryl or heteroaryl;

$R^3$ is
(1) a nitrogen-containing heterocycloalkyl or heteroaryl group, wherein said heteroaryl group can have up to two additional substituents;
(2) an aryl or aralkyl group having one or two nitrogen-containing substituents selected from the group consisting of amino, monoalkylamino, dialkylamino, trialkylammonium salts, and acylamino, wherein said aryl or aralkyl group can have up to two additional substituents; or
(3) a $C_1$ to $C_{10}$ alkyl, $C_2$ to $C_{10}$ alkenyl, or $C_5$ to $C_7$ cycloalkyl group having one or two nitrogen-containing substituents selected from the group consisting of amino, monoalkylamino, dialkylamino, trialkylammonium salts, acylamino, arylcarbonylamino and ureido; or a pharmaceutically-acceptable salt thereof;
with the provisos that R is not substituted or unsubstituted n-propyl; that when R is t-butyl and $R^1$ and $R^2$ are both hydrogen, then $R^3$ can not be 3-aminopropyl or 3-(t-butoxycarbonylamino)propyl; that when R is isopropyl and $R^1$ and $R^2$ are both hydrogen, then $R^3$ can not be 2-amino-6-chlorophenyl or 8-(3,7-dichloroquinoline); and that when R is isopropyl, $R^1$ is hydrogen, and $R^2$ is methyl, then $R^3$ can not be 4-(methylamino) cyclohexane.

2. The compound of claim 1, wherein

R is $C_3$ to $C_6$ alkyl, alkenyl or alkynyl, any of which can be optionally substituted with aryl, heteroaryl, halo, alkyl, alkoxy, hydroxy, amino, cyano, nitro, trifluoromethyl, acylamino or carbamoyl; and $R^3$ is
  (1) a nitrogen-containing heterocycloalkyl or heteroaryl group, wherein said heteroaryl group can have up to two additional substituents;
  (2) an aryl or aralkyl group having one nitrogen-containing substituent selected from the group consisting of amino, monoalkylamino, dialkylamino, trialkylammonium salts, acylamino, arylcarbonylamino, and alkoxycarbonylamino, wherein said aryl or aralkyl group can have up to one additional substituent; or
  (3) a $C_1$ to $C_{10}$ alkyl, $C_2$ to $C_{10}$ alkenyl, $C_3$ to $C_{10}$ alkynyl or $C_3$ to $C_7$ cycloalkyl group having one nitrogen-containing substituent selected from the group consisting of amino, monoalkylamino, dialkylamino, trialkylammonium salts, acylamino, arylcarbonyl amino and alkoxycarbonylamino.

3. The compound of claim 2, wherein $R^2$ is H.

4. A compound represented by the formula:

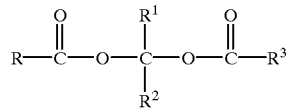

wherein

R is n-propyl which can be optionally substituted with aryl, heteroaryl, halo, alkyl, alkoxy, amino, hydroxy, cyano, nitro, trifluoromethyl, acylamino or carbamoyl;

$R^1$ and $R^2$ are independently H, $C_3$–$C_{10}$ alkyl, $C_2$–$C_{10}$ alkenyl, or $C_2$–$C_{10}$ alkynyl, any of which can be optionally substituted with halo, alkoxy, amino, trifluoromethyl, aryl or heteroaryl;

$R^3$ is
  (1) a nitrogen-containing heterocycloalkyl, heterocycloalkenyl, heteroaryl group or heteroaralkyl group or an alkylammonium salt thereof, wherein said heteroaryl group and said heteroaralkyl group can have up to two additional substituents;
  (2) an aryl or aralkyl group having one or two nitrogen-containing substituents selected from the group consisting of amino, monoalkylamino, dialkylamino, trialkylammonium salts, acylamino, arylcarbonylamino, alkoxycarbonylamino, formamido, guanidino, ureido, sulfamyl, and alkylsulfonamido, wherein said aryl or aralkyl group can have up to two additional substituents; or
  (3) a $C_1$ to $C_{10}$ alkyl, $C_2$ to $C_{10}$ alkenyl, $C_3$ to $C_{10}$ alkynyl or $C_3$ to $C_7$ cycloalkyl group having one or two nitrogen-containing substituents selected from the group consisting of amino, monoalkylamino, dialkylamino, trialkylammonium salts, acylamino, arylcarbonylamino, alkoxycarbonylamino, formamido, guanidino, ureido, sulfamyl, and alkylsulfonamido; or a pharmaceutically-acceptable salt thereof;

with the proviso that when $R^3$ is $C_1$ to $C_{10}$ alkyl, then said nitrogen-containing substituent can not be amino.

5. The compound of claim 4, wherein $R^1$ and $R^2$ are independently H, lower alkyl, lower alkenyl or lower alkynyl; and $R^3$ is
  (1) a nitrogen-containing heterocycloalkyl or heteroaryl group, wherein said heteroaryl group can have up to two additional substituents;
  (2) an aryl or aralkyl group having one nitrogen-containing substituent selected from the group consisting of amino, monoalkylamino, dialkylamino, trialkylammonium salts, acylamino, arylcarbonylamino, and alkoxycarbonylamino, wherein said aryl or aralkyl group can have up to one additional substituent; or
  (3) a $C_1$ to $C_{10}$ alkyl, $C_2$ to $C_{10}$ alkenyl, $C_3$ to $C_{10}$ alkynyl or $C_3$ to $C_7$ cycloalkyl group having one nitrogen-containing substituent selected from the group consisting of amino, monoalkylamino, dialkylamino, trialkylammonium salts, acylamino, arylcarbonylamino and alkoxycarbonylamino.

6. The compound of claim 4, wherein

R is n-propyl;

$R^1$ is H or lower alkyl and $R^2$ is H; and $R^3$ is
  (1) a nitrogen-containing heteroaryl group, wherein said heteroaryl group can one additional substituent;
  (2) an aryl group having one nitrogen-containing substituent selected from the group consisting of amino, monoalkylamino, dialkylamino, trialkylammonium salts, and wherein said aryl group can have up to two additional substituents; or
  (3) a $C_1$ to $C_{10}$ alkyl group having one nitrogen-containing substituent selected from the group consisting of acylamino, arylcarbonylamino and alkoxycarbonylamino.

7. The compound of claim 6, wherein said compound is 4-(butyramido)butyroyloxymethyl butyrate, 4-(butyramido)benzoyloxymethyl butyrate, 4-amino benzoyloxymethyl butyrate, 4-aminobenzoyloxymethyl butyrate hydrochloride, 1-(4-aminobenzoyloxy)ethyl butyrate, 3-pyridinecarboxymethyl butyrate, 1-(3-pyridinecarboxy)ethyl butyrate, or (N-methylpyridinium)-3-carboxymethyl butyrate chloride.

8. A pharmaceutical composition comprising a therapeutically-effective amount of a compound of any one of claims 1 to 7 and a pharmaceutically-effective carrier or diluent.

9. A pharmaceutical composition comprising a therapeutically-effective amount of a compound of any one of claims 1 to 7 with a therapeutically-effective amount of a pharmaceutical agent, wherein said agent is selected from the group consisting of a cytokine, an interleukin, an anti-cancer agent or anti-neoplastic agent, a chemotherapeutic agent, an antibody, a conjugated antibody, an immune stimulant, an antibiotic, a hormone antagonist or a growth stimulant.

10. The composition of claim 9 wherein said pharmaceutical agent comprises a cytotoxic agent.

11. The composition of claim 9 wherein said antibiotic is an antiviral nucleoside antibiotic selected from the group consisting of ganciclovir, acyclovir, and famciclovir.

12. The composition of claim 9 wherein said antibiotic is ganciclovir.

13. The composition of claim 9 wherein said chemotherapeutic agent is selected from the group consisting of alkylating agents, purine and pyrimidine analogs, vinca and vinca-like alkaloids, etopsides and etopside-like drugs, corticosteroids, nitrosoureas, antimetabolites, platinum based cytotoxic drugs, hormonal antagonists, anti-androgens and antiestrogens.

14. The composition of claim 9 wherein said cytokine is an interferon.

15. The composition of claim 9 wherein said immune stimulant is *Corynebacterium parvum* or a sarcolectin.

16. The method of claim 9 wherein the chemotherapeutic agent is selected from the group consisting of tamoxifen, doxorubicin, L-asparaginase, dacarbazine, amsacrine, procarbazine, hexamethylmelamine, mitoxantrone and gemcitabine.

* * * * *

UNITED STATES PATENT AND TRADEMARK OFFICE
CERTIFICATE OF CORRECTION

PATENT NO.   : 6,110,970
DATED        : August 29, 2000
INVENTOR(S)  : Nudelman et al.

It is certified that error appears in the above-identified patent and that said Letters Patent is hereby corrected as shown below:

Column 2,
Line 23, change "Stamatoyannopouos" to -- Stamatoyannopolous --;
Line 33, change "buryric" to -- butyric --;
Line 45, change "*Biotechniaues*" to -- *Biotechniques* --;

Column 8,
Line 21, change "under going" to -- undergoing --;

Column 10,
Line 2, after "AmBOMB•HCl" insert -- , --;

Column 25,
Line 34, change "evaluted" to -- evaluated --; and

Column 26,
Line 9, change "erthroblastic" to -- erythroblastic --.

Signed and Sealed this

Nineteenth Day of March, 2002

Attest:

JAMES E. ROGAN
Director of the United States Patent and Trademark Office

*Attesting Officer*